United States Patent [19]
Hercend et al.

[11] Patent Number: 5,830,758
[45] Date of Patent: Nov. 3, 1998

[54] ISOLATED Vβ TCR ANTIBODIES

[75] Inventors: Thierry Hercend, Nogent-sur Marne; Frederic Triebel, Seine; Sergio Roman-Roman; Laurent Ferradini, both of Paris, all of France

[73] Assignee: Roussel Uclaf, France

[21] Appl. No.: 437,353

[22] Filed: May 9, 1995

Related U.S. Application Data

[62] Division of Ser. No. 423,383, Apr. 14, 1995, Pat. No. 5,700,907, which is a continuation of Ser. No. 934,530, filed as PCT/FR92/00130, Feb. 12, 1992, published as WO92/13950, Aug. 20, 1992, abandoned.

[30] Foreign Application Priority Data

Feb. 12, 1991 [FR] France ................................. 91 01613
Apr. 12, 1991 [FR] France ................................. 91 04523

[51] Int. Cl.$^6$ ................................................. C07K 16/28
[52] U.S. Cl. ................. 435/331; 530/388.22; 530/387.9; 530/388.75; 435/334
[58] Field of Search .................. 530/387.9, 388.75, 530/391.3, 391.7, 388.22; 435/240.27, 331, 334; 424/139.1

[56] References Cited

U.S. PATENT DOCUMENTS 5,223,426 6/1993 Skibbens et al. ....................... 435/331

OTHER PUBLICATIONS

Goverman et al. in Basic and Clinical Immunology, Stites et al. (ed), pp. 73–77, 1991.

Chien et al. Immunology Today 14(12) 597–602, 1993.

Kimura et al. Eur. J. Immunol. 17, 375–383, 1987.

Choi et al. Nature 346, 471–473, 1990.

George et al. EMBL/Geubank/DDBJ databases. Locus: HSTVB55, 1990.

Plaza et al. EMBL/Geubank/DDBJ databases. Locus: HSV71RNA, 1991.

Plaza et al. EMBL/Geubank/DDBJ databases. Locus: HSV91RNA, 1991.

Hinukaneu et al. EMBL/Geubank/DDBJ databases. Locus: HSTCRBBBC, 1991.

*Primary Examiner*—Stephen Walsh
*Assistant Examiner*—Karen E. Brown
*Attorney, Agent, or Firm*—Bierman, Muserlian and Lucas

[57] ABSTRACT

An isolated antibody that specifically binds a peptide coded by a nucleotide sequence coding for a variable region of β-chain of an human T lymphocyte receptor, said nucleotide sequence having a nucleotide sequence selected from any of:

the nucleotide sequences of SEQ ID Nos. 2 to 19.

2 Claims, 14 Drawing Sheets

```
                GTAAAGCTCCCATCCTGCCCTGACCCTGCC  ATGGGGACCAGCCTCCTCTGCTGTGGATGCCCTCTGTCTCC................TTGGGGGCAGATCA
                                                  1
HT11            ..............................  ........C.....................................................
PH22            ..............G...............  ..............................................................
CDS1            ..............................  ...........C..................................................
HT116           ..............................  ...............C.........G.....T..GG..T..C..A...A.............
AT122           ..............................  ...............C.........G.....T..GG..T..C..A...A.............
IGRb11          ..............................  ...............T.A.......G.....T..G....T..C..................
PH16            ..............................  ...............C.........G.....T..G....T..C..................
GLPA            ..............................  ...............C.........G.....T..G....T..C..................
HT45            ..............................  ...............C.........G.....T..G....T..C..................
HBP50           ..............................  ...............................G.CTCCA.........................

CGCAGATACTGGAGTCTCCCCAGAACCCCAGACACAAGATCACAAAGAGGGGACAGAATGTAACTTTCAGGTGTGATCCAATTTCTGAACACAACCGCCTT
                                                                                100
HT11            ....................................................C.......................................
PH22            G.AGATAT......................................................................................
CDS1            ..............................................................................................
HT116           ..............................................................................................
AT122           ................TC..T..GT......A.............G..C..........................G.GT..TGTATC.......
IGRb11          ................TCT..GT......................G..C..........................G.GT..TGTATC.......
HBP25           ..............................................G..C..................C.....G.GT..TGTATC.......
IGRb12          ..............................................G..C..........................G.GT..TGTATC.......
PH16            .A...G.G......................A..GAGC......A...G..A..........................A.GT..T..CTGC....
GLPA            .A...GAG......................TC....GAGC...A...G..A..........................A.GT..T..CTGC....
HT45            .A...GAG......................TC....GAGC...A...G..A..........................A.GT..T..CTGC....
HBP50           .A...GAG......................TC....GAGC...A...G..A..........................A.GT..T..CTGC....
HBMLT           .A...G.G......................TC.....GAGC..A...G..A..AT....GAGC.............A.GT..T..CTGC....
                                                                                            TGGGAGC.
```

```
             1
PH27    CAACTTGTGCCCTTTGTCTCCTGTGGACAGGACACATGGATGGATGCTGGAATCACCC
PL4.2
IGRb13            T.........G....----....A........

100
PH27    AGAGCCCAAGACACAAGGTCACAGAGACAGGAACACCAGTGACTCTGAGATGTCACCA
PL4.2                                       ............................
IGRb13  .................A...............GG.AG.....CT..GCG........

PH27    GACTGAGAACCACCGCTATATGTACTGGTATCGACAAGACCCGGGGCATGGGCTGAGG
PL4.2   ....................C....................................
IGRb13  ....TG.......AA.A......T................T...A............

200
PH27    CTGATCCATTACTCATATGGTGTTAAAGATACTGACAAAGGAGAAGTCTCAGATGGCT
PL4.2   ..A.......................................................
IGRb13  ......................C....C...A..........................

PH27    ATAGTGTCTCTAGATCAAAGACAGAGGATTTCCTCCTCACTCTGGAGTCCGCTACCAG
PL4.2   .........................................................-........
IGRb13  .C................C........CC...C...............T...G..TC

300
PH27    CTCCC-AGACATCTGTGTACTTCTGTGCCATCAGC  324
PL4.2   .....G........................CT..A  237
IGRb13  .....-..........A..T.....C....G...G  294
```

```
         1
IGRb14  AGAAGACCCCTCCATCCTGTAGCACCTGCCATGAGCCATCGGGCTCCTGTGCTGTGTGGCCTTTTCTCTCCTGTGTGGGCAAGTCCAGTGAATGCTGGTGT
IGRb15  .........TG.T........A..A.........................................................G.......T......GA.
IGRb16                      aaggcccagccccttcattgggctgcagcatcagctgtttccttcctgcag..............G..............
HBVP34  ...............................................CA...G..........................G..................
CEM     ...................CG..TT..........C..........................G...................................

IGRb14  CACTCAGACCCCAAAATTCCAGGTCCTGAAGACAGAGGACATGACACTGCAGTGTGCCCAGGATATGAACCATAACTCCATGTACTGGTATCGAC
IGRb15  ..C....C...G.A....C..CT...A...GCAG......G.C.........AGA..A........GA....TG...............A...
IGRb16  ................................GCA......T...................................................
HBVP34  .........................................................A......................G.A.A....C..
CEM     ................................G..................T............................G.A.A.......

IGRb14  AAGACCCAGGCATGGGACTGAGGCTGATTTATTACTCAGGTTCTGAGGGTACCACTGACAAAGGAGAAGTCCCCAATGGCTACAATGTCTCCAGATTA
IGRb15  ....T..T..AC....G..A.....C..CC....T...AA..A...CA.........G..........TG..T..T.G...........GC.
IGRb16  .........G.....A.........C........T....T.GG..CT...T......T.........G.........C............C.
HBVP34  .........G.........-G.............C....T.GG..CT...T......C..........................C.
CEM     .........G............-G..............C.......T.GG................A....C.......G.....TG........C.

300
IGRb14  AACAAACGGGAGTTCTCGCTCAGGCTGGAGTCGGCTGCCTCCCTCCCAGACATCTGTGTACTTCTGTGCCAGCACC  339
IGRb15  ...C..GAT..T...C.C....C..CT...C...T...TA....T.....................GT       339
IGRb16  .C...C.GA...T..C..........C....T.................CT.....................GT 345
HBVP34  .C...C.GA...T..C..........C....T.................CT.....................GT 339
CEM     ....A....A..A.T....CT...GG..T...................A..........................G.. 339
```

IGRb20 ATCCTGCCCTGGGCCTTGCCTGGTCTGCCTGATCTGCCTCACTCTGCCTGTCTGCCTGATCTGCCTCACTCTGCTGCAGGCTCCTCTGCTGTGGTCTTCTGCCTCCTCCCAAGCAGGTCCCTTGGACA

IGRb20 CAGCTGTTTCCCAGACTCCAAAATACCTGGTCACACAGATGGGAAACGACAAGTCCATTAAATGTGAACAAAATCTGGGCCATGATACTATGTATTGGTA
PL2.6 ...G..T...

IGRb20 TAAACAGGACTCTAAGAAATTTCTGAAGATAATGTTTAGCTACAATAATAAGGAGCTCATTATAAATGAAACAGTTCCAAATGCCTTCTCACCTAAATCT
PL2.6 ...

IGRb20 CCAGACAAAGCTCACTTAAATCTTCACATCAATTCCCTGGAGCTTGGTGACTCTGCTGTGTATTTCTGTGCCAGCAGC 339
P12.6 ...  246

FIG. 6

ISOLATED Vβ TCR ANTIBODIES

PRIOR APPLICATION

This application is a division of U.S. patent application Ser. No. 423,383 filed Apr. 14, 1995 now U.S. Pat. No. 5,700,907, which is a continuation of U.S. patent application Ser. No. 934,530 filed Nov. 23, 1992, now abandoned, which is a 371 of PCT application FR 92/00130 filed Feb. 12, 1992, published as WO92/13950 Aug. 20, 1992.

The present invention relates to new nucleotide sequences coding for variable regions of β chain T-cell receptors, corresponding peptide segments and the diagnostic and therapeutic uses.

It is known that the receptors recognizing antigens at the surface of mature T lymphocytes (hereafter designated T-cell receptors) possess a structure having a certain similarity with those of immunoglobulins. Therefore, they contain heterodimeric structures containing α and β glycoprotein chains or γ and δ glycoprotein chains (see Meuer et al. (1), Moingeon et al. (2), Brenner et al. (3), Bank et al. (4)).

The directory of T-cell receptors must be able to address the immense diversity of antigenic determinants. This is obtained by genetic recombination of different discontinuous segments of genes which code for the different structural regions of T-cell receptors. Thus, the genes contain V segments (variable segments), optionally D segments (diversity segments), J segments (junction segments) and C segments (constant segments). During the differentiation of T-cells, specific genes are created by recombination of V, D and J segments for the β and δ loci and V and J segments for the α and β loci. These specific combinations as well as the pairing of two chains create the combinational diversity. This diversity is highly amplified by two supplementary mechanisms, namely the imprecise recombination of V-D-J or V-J segments and the addition of nucleotides corresponding to the N region (Davis et al. (5)).

A certain number of genetic V segments are already known. These segments have been grouped into subfamilies as a function of the similarity of sequences. By definition, the segments which have more than 75% similarity in the nucleotide sequence have been considered as members of the same subfamily (Crews et al. (6)). At present, about 60 distinct Vβ genetic segments are known (Wilson et al. (7), Robinson (8), Leider et al. (9), Reynolds (10), Li et al. (11)) which have been classified into 20 subfamilies, 7 of which have only one member (see Wilson et al. already quoted).

Furthermore, monoclonal antibodies directed against specific segments of the variable parts of T-cell receptors, in particular the β or δ chains, were recently described in WO 90/06758. These monoclonal antibodies are useful not only as diagnostic tools but also as therapeutic tools, for example, vis-à-vis rheumatoid athritis.

The use of synthetic peptides corresponding to the variable regions of the α or β chains in the treatment of auto-immune diseases was also described (27 and 28).

It is also known that variations exist from one individual to another in the expression of different variable segments of the T-cell receptor in man (27 and 28).

The present invention aims to enrich the directory of genetic segments coding for the variable regions of the β chains of T-cell receptors by providing new Vβ genetic segments belonging to new subfamilies or belonging to subfamilies of which at least one member is already known.

Therefore a subject of the present invention is nucleotide sequences coding for the variable regions of β chains of human T lymphocyte receptors, corresponding to cDNAs containing nucleotide sequences chosen from any one of the Vβ segments corresponding to one of the sequences SEQ ID No. 2 to 19, and the sequences which differ from them by one or more nucleotides.

More particularly a subject of the present invention is: sequences coding for the variable regions of β chains of human T lymphocyte receptors, corresponding to cDNAs containing nucleotide sequences chosen from any one of the Vβ segments corresponding to one of the sequences SEQ ID No. 2 to 5, and the sequences which differ from them by one or more nucleotides.

The expression "and sequences which differ from them by one or more nucleotides", encompasses alleles which differ by up to 8 nucleotides, but more often differ by 1 or 2 nucleotides, or which can differ by the deletion or addition of one or two codons.

Also a more particular subject of the invention is:

nucleotide sequences coding for the variable regions of β chains of human T lymphocyte receptors, corresponding to cDNAs corresponding to all or part of the nucleotide sequences chosen from any one of the Vβ segments corresponding to one of the sequences SEQ ID No. 2 to 5, and the sequences which differ from them by one or two nucleotides, nucleotide sequences coding for the variable regions of the β chains of human T lymphocyte receptors, corresponding to cDNAs corresponding to one of the nucleotide sequences chosen from any one of the Vβ segments corresponding to one of the sequences SEQ ID No. 6 to 15, the sequences which differ from them by one or two nucleotides and fragments of the latter, in particular, the fragments of sequences which correspond to all or part of the nucleotide sequences chosen from any one of the V segments corresponding to one of the sequences:

1 to 155 of SEQ ID No. 8
1 to 125 of SEQ ID No. 9
1 to 111 of SEQ ID No. 10 and the sequences which differ from them by one or two nucleotides, nucleotide sequences coding for the variable regions of the β chains of human T lymphocyte receptors, corresponding to cDNAs corresponding to all or part of the nucleotide sequences chosen from any one of the Vβ segments corresponding to one of the sequences:

1 to 195 of SEQ ID No. 16
1 to 99 of SEQ ID No. 17
1 to 113 of SEQ ID No. 18
1 to 186 of SEQ ID No. 19, and the sequences which differ from them by one or two nucleotides.

By the expression "nucleotide sequences corresponding to cDNAs corresponding to all or part of the nucleotide sequences" is also designated the complete sequences as well as fragments of these sequences, including short fragments which can be used as probes (generally containing at least 10 nucleotides) or as primers (generally containing at least 15 nucleotides). In a general fashion, the present invention encompasses the group of new oligonucleotides which are fragments of Vβ sequences according to the invention.

As for the sequences which differ by one or two nucleotides, they correspond to variations which are observed experimentally at the time of determination of the nucleotide sequence of several cDNAs.

Also a subject of the present invention is the peptides coded by the nucleotide sequences according to the invention as well as the alleles and the derivatives of the latter which have the same function.

In a general fashion, the present invention encompasses the peptides constituted by or composed of a peptide sequence coded by the nucleotide sequences according to the invention as well as fragments of these peptides. It also encompasses the peptides which differ from the latter by one or more amino acids and which have the same function. These peptides can correspond to modifications such as those known with muteins or to allelic variations. In fact it has been shown in particular that certain genetic segments coding for the variable regions of chains of T receptors in man were subjected to a phenomenon of genetic polymorphism called allelic variation (29). The present invention encompasses the peptides resulting from this phenomenon.

The nucleotide sequences according to the invention have been obtained according to the following stages:
- isolation of the RNAs of peripheral lymphocytes of an individual;
- obtaining the complementary DNA using reverse transcriptase and a primer A which is specific to the Cβ region (SEQ ID No. 20);
- genetic amplification (by Anchored Polymerase Chain Reaction or A-PCR) using a DNA polymerase, a poly C primer (SEQ ID No. 21) and a primer B which is specific to the Cβ region (SEQ ID No. 22);
- a new amplification by A-PCR using DNA polymerase and a primer C which is specific to the Cβ region (SEQ ID No. 23);
- insertion in a plasmid vector;
- transformation of a bacterial host with the recombinant vector;
- screening of recombinant bacterial colonies with a labelled oligonucleotide D which is specific to Cβ (SEQ ID No. 24);
- extraction of plasmids from positive colonies;
- and sequencing of DNA fragments containing the Cβ region.

The present invention can be reproduced, in particular, by bispecific genetic amplification (polymerase chain reaction or PCR) by starting with the peripheral lymphocytes which express the mRNAs including the variable or junctional β segments corresponding to sequences ID No. 2 to 19 of the invention or alternatively by applying this PCR technique to genomic DNA of any somatic cell of an individual taken at random. The invention can also be reproduced by preparing the above genetic sequences by the chemical synthesis of oligonucleotides.

The peptides according to the invention can be obtained by standard peptide synthesis. They can also be obtained by the application of known genetic engineering techniques including the insertion of a DNA sequence coding for a peptide according to the invention into an expression vector such as a plasmid and the transformation of cells with this expression vector.

Therefore a subject of the present invention is also plasmids and expression vectors containing a DNA sequence coding for a peptide according to the invention as well as the hosts transformed with this vector.

Also a subject of the present invention is antibodies, and, in particular, monoclonal antibodies, directed against an antigenic determinant belonging to or composed of a peptide according to the invention.

The monoclonal antibodies may be obtained by any of the techniques which allow the production of antibody molecules from cell line culture. These techniques include different techniques using hybridomas.

The antibody production may be obtained in animals by the immunization of the animals by injection with the peptides or fragments according to the invention, whether they be natural, recombinant or synthetic, optionally after coupling to an immunogen such as tetanus anatoxin, or also by injection of human T lymphocytes expressing the corresponding sequences at their surface, including recombinant cells transfected with the corresponding coding sequences.

Also a subject of the present invention is hybridomas producing monoclonal antibodies directed against the polypeptides according to the invention.

The present invention also encompasses the fragments and the derivatives of monoclonal antibodies according to the invention which are reactive with defined variable regions of T-cell receptors. These fragments are, in particular, the $F(ab')_2$ fragments which can be obtained by the enzymatic cleavage of antibody molecules with pepsin, the Fab' fragments which can be obtained by reduction of the disulphide bridges of $F(ab')_2$ fragments and the Fab fragments which can be obtained by the enzymatic cleavage of antibody molecules with papain in the presence of a reducing agent. The fragments can also be obtained by genetic engineering.

The monoclonal antibody derivatives are for example antibodies or fragments of these antibodies to which labellers such as a radio-isotope are attached. The monoclonal antibody derivatives are also antibodies or fragments of these antibodies to which therapeutically active molecules are attached, in particular, cytotoxic compounds.

The products of the invention have several uses in the field of diagnostics and in the field of therapeutics.

1—Uses in the field of diagnostics

The oligonucleotides contained in the nucleotide sequences according to the invention can be used to constitute detection probes (generally at least 10 nucleotides) which are capable of hybridizing with a variable region of a β chain or primers for the amplification of DNA (generally containing at least 15 nucleotides and preferably at least 17 nucleotides) which are capable of being linked to a sequence to be amplified.

Thus the oligonucleotides can be used in the diagnosis of immune disorders by detecting the presence of nucleic acid sequences which are homologues of a gene coding for the variable regions of β chains of T-cell receptors in the mRNA of a sample from a patient. Different methods can be used to establish a connection between the expression of T-cell genes and an illness. These methods include:

a—the production and analysis of cDNA expression libraries obtained from T-cells connected with the illness to determine the frequency of dominant genes;

b—Southern blot analysis of samples of genomic DNA to determine whether genetic polymorphisms or rearrangements of the genes coding for the T-cell receptors exist;

c—the analysis of samples by obtaining cDNA, amplification by PCR and hybridization with labelled probes;

d—the hybridization in situ of T-cells without culture of T-cells beforehand.

The primers can be used in PCR reactions in a method such as that defined in c.

The monoclonal antibodies, the fragments or the derivatives of these antibodies according to the invention can be used to study T-type immune responses, for example in the field of the auto-immune diseases of cancerology, of allergies, of transplants and of infectious diseases. In particular, the directory of different variable β segments of the T receptor can be studied, whether it be blood or tissue T-cells. In a general fashion the techniques used can be in vitro or in vivo methods.

With in vitro methods, the samples used can be samples of body fluids or tissue samples. The techniques used can include in particular flow cytofluorimetry to analyse blood T lymphocytes or labelling with immunoperoxidase on an anatomopathological section to study the lymphocytes infiltrating the tissues.

With in vivo methods, the antibodies, their fragments or their derivatives are administered by the usual routes, for example by intravenous route, and the immunospecific linkages are detected. This can be obtained for example in the case where an antibody is used which is labelled with a radio-isotope.

2—Uses in the therapeutic field

The oligonucleotides contained in the nucleotide sequences according to the invention can be used in therapeutics as anti sense oligonucleotides. In fact it is known that it is possible in vitro to inhibit the expression of a transcript gene in human lymphocytes by incubating these lymphocytes with an anti sense oligonucleotide specific to the gene in question (30). These anti sense oligonucleotides generally contain at least 10 and, preferably, at least 16 nucleotides. These anti sense oligonucleotides can be in particular the inverted and complemented sequences corresponding to 20 nucleotides upstream from the initiation site of the translation (ATG). The significance of the use in vitro of anti sense oligonucleotides specific to a Vβ genetic segment is to abolish (or strongly diminish) the expression of a T receptor containing this Vβ segment and thus to obtain a phenomenon of clonal deletion at the level of the specific reactivity of T lymphocytes. The anti sense oligonucleotides can not only be used in vitro on human T lymphocytes which are then reinjected, but also in vivo by local or systemic injection preferably after modification to increase the stability in vivo and the penetration into the lymphocytes of these oligonucleotides.

The monoclonal antibodies according to the invention can be used to modulate the immune system. It is in this way that the antibodies can be administered to block the interaction of the effector T-cells with their specific antigen. Anti T receptor antibodies linked for example to a cytotoxic molecule or a radio-isotope can also be administered so as to obtain a clonal deletion, thanks to the specific fixation on a β chain of a T-cell receptor. The monoclonal antibodies according to the invention can be used in therapeutics at low mitogenic concentrations so as to activate, in a specific fashion, certain sub-assemblies of T-cells or can be used at much higher concentrations to fix them to the receptors concerned and thus label these sub-assemblies with a view to their elimination by the reticulo-endothelial system. An important criterion in the treatment of an illness is the ability to modulate the sub-assemblies of T-cells linked with an illness. The exact nature of this therapeutic modulation, namely blocking or suppressing a particular sub-assembly of T-cells or on the contrary stimulating and activating a particular sub-assembly, will depend on the illness in question and the specific sub-assembly of T-cells concerned.

This type of treatment has an advantage over current treatments using antibodies such as the treatment with anti CD3 antibodies in patients having had a kidney transplant and having a rejection problem, given that thanks to the invention there will be no modulation of the totality of the T-cell population but only of the sub-assembly of T-cells expressing the β sub-family specific to the T-cell receptors.

Moreover, as the response of T-cells is often oligoclonal, it is generally convenient to use "cocktails" of several antibodies in therapeutics.

In addition anti Vβ antibodies can be used to select T lyphocytes in vitro, for example by passing through a column containing spheres carrying the antibody. This separation of certain T lymphocytes can be used with a view to culturing these lymphocytes before reinjection into the patient.

Moreover, all or part of the peptide sequences according to the invention can be used in therapeutics, that is to say the peptide sequences coded by the nucleotide sequences according to the invention or fragments of these sequences (generally containing at least 8 to 10 amino acids). These sequences or fragments, administered to humans or animals, can act as a decoy, that is to say they fix themselves on the epitope carried by the harmful antigen and stop the reaction of normal T-cells with the antigen, preventing in this way the development of an illness which is aggressive towards the self determinants. They can also be used as immunogens in the manufacture of vaccines (optionally after conjugation with protein carriers).

The invention will be described in greater detail hereafter by referring to the annexed figures in which:

BREIF DESCRIPTION OF THE DRAWINGS

FIG. 1 shows in a line both known Vβ5 sequences and partial sequences of new sequences according to the invention marked IGRb08 (SEQ ID No. 8), IGRb09 (SEQ ID No. 9), IGRb06 (SEQ ID No. 6) and IGRb07 (SEQ ID No. 7) belonging to known Vβ5 sub-family. In this figure, the numbering of nucleotides starts at the ATG initiation codon (which is underlined). The dots indicate identical nucleotides. The sequence which is assumed to be the leader sequence has a line over it.

FIGS. 2 and 2(A) show in a line both known Vβ6 sequences and partial sequences of new sequences according to the invention marked IGRb11 (Seq. ID. No. 10) and IGRb12 (SEQ ID. No. 11) belonging to known Vβ6 sub-family. In this figure, the numbering of nucleotides starts at the ATG initiation codon (which is underlined). The dots indicate identical nucleotides.

FIG. 3 shows in a line both known Vβ12 sequences and partial sequence of new sequence according to the invention marked IGRb13 (SEQ ID No. 12) belonging to known Vβ12 sub-family. In this figure, the numbering of nucleotides starts at the 5' end of PH27. The dots indicate identical nucleotides. The sequence which is assumed to be the leader sequence has a line over it.

FIG. 4 shows in a line both known Vβ13 sequences and partial sequences of new sequences according to the invention marked IGRb14 (SEQ ID No. 13), IGRb15 (Seq. ID No. 14) and IGRb16 (SEQ ID No. 15) belonging to known Vβ13 sub-family. In this figure, the numbering of nucleotides starts at the ATG initiation codon (which is underlined). The dots indicate identical nucleotides. The sequence which is assumed to be the leader sequence has a line over it.

FIG. 5 shows in a line both known Vβ7 sequences and partial sequences of new sequences according to the invention marked IGRb17 (SEQ ID No. 16), IGRb18 (SEQ ID No. 17) and IGRb19 (SEQ ID No. 18) belonging to known Vβ7 sub-family. In this figure, the numbering of nucleotides starts at the ATG initiation codon (which is underlined). The dots indicate identical nucleotides. The sequence which is assumed to be the leader sequence has a line over it.

FIG. 6 shows in a line both the known Vβ9 sequence and a partial sequence of a new sequence according to the invention marked IGRb20 (SEQ ID NO: 19) belonging to the known Vβ9 sub-family. In this figure, the numbering of the nucleotides starts at the ATG initiation codon (which is underlined). The dots indicate identical nucleotides. The sequence which is assumed to be the leader sequence has a line over it.

FIG. 7 shows the Southern blot analyses of the genomic DNA treated with a restriction enzyme using probes specific to Vβ sub-families. The restriction enzymes used are EcoRI (column R), Hind III (column H) and Bam I (column B). On this figure the triangles mark the position of DNA fragments hybridizing in a specific fashion with Cβ.

The reactivity-control for NKTa or $OKT_3$ antibodies is given for each type of cell respectively.

The number of cells counted (linear scale) is given as a function of the intensity of fluorescence (logarithmic scale).

Figure 9A:
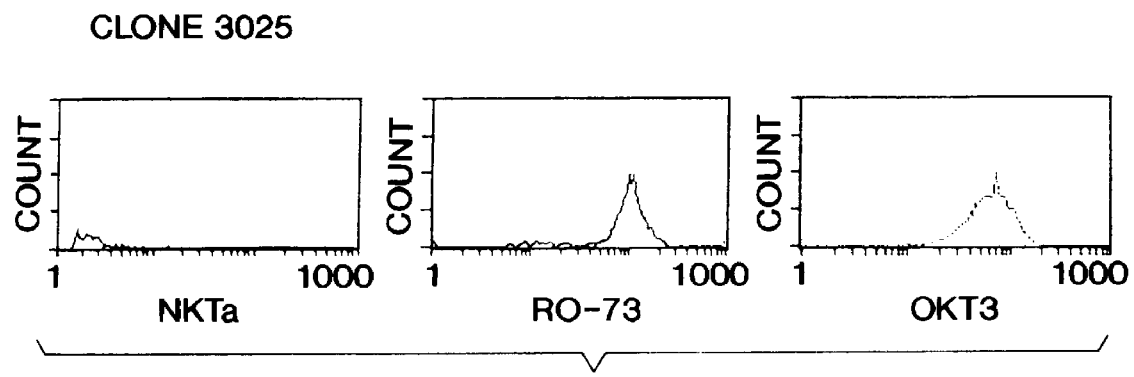
FIGS. 9 (A–C) represent the analysis by cytofluorimetry of the reactivity of the monoclonal antibody RO-73 vis-à-vis the immunizing clone 3025 (FIG. 9A), clone 12410 (FIG. 9B) and circulating lymphocytes (FIG. 9C) respectively.
Figure 9B:
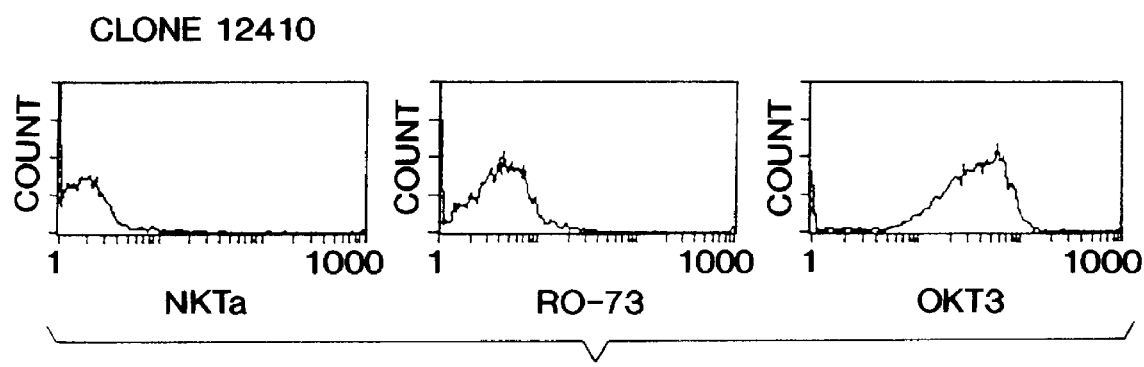
Figure 9C:
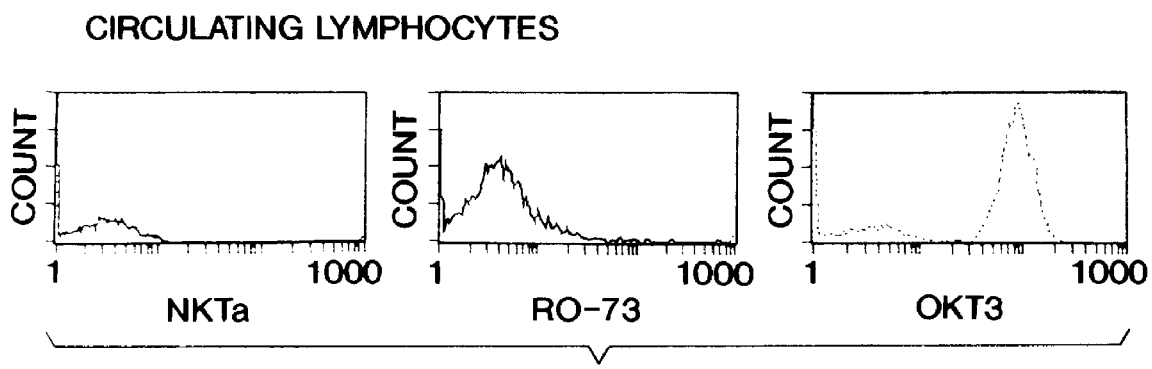
Figure 10A:
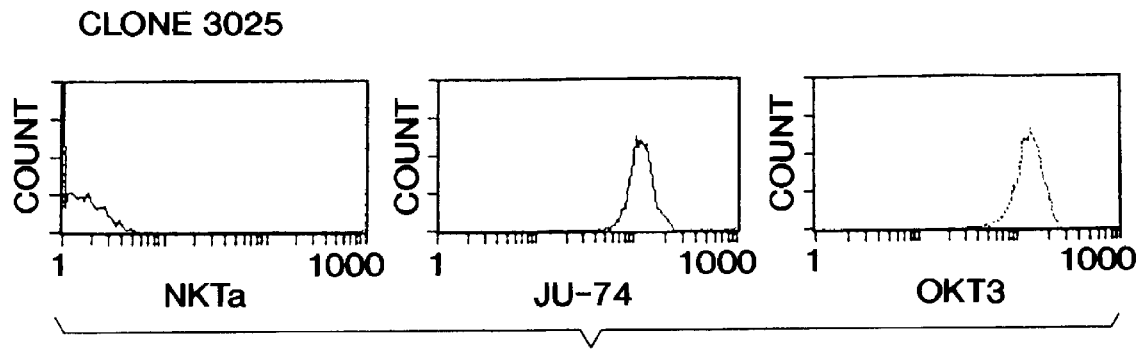
Figure 10B:
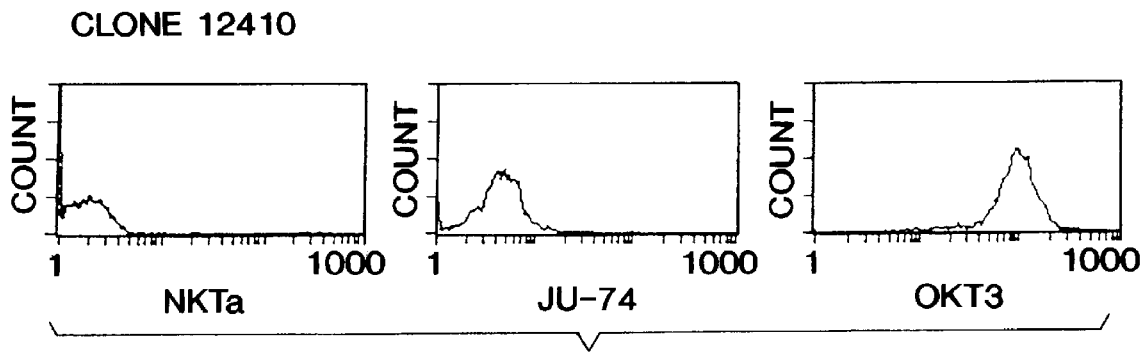
Figure 10C:
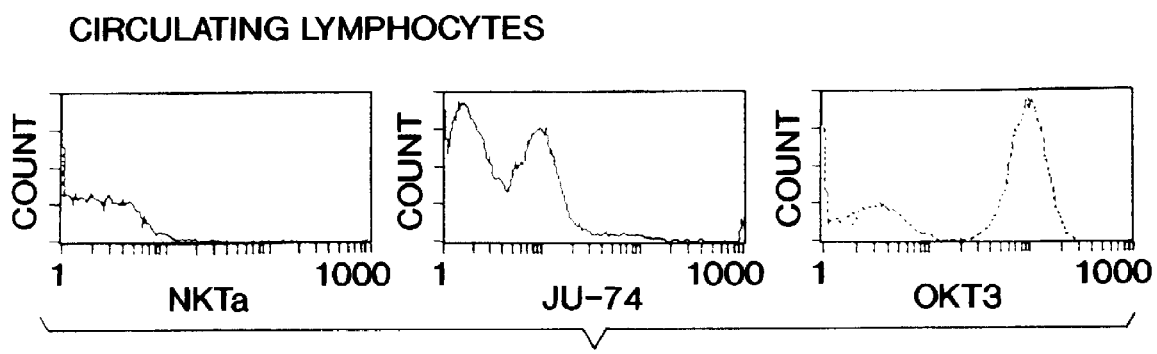

FIG. 10 (A–C) represent the analysis by cytofluorimetry of the reactivity of the monoclonal antibody JU-74 (FIG. 10A, 10B, 10C: same conditions as for FIG. 9A, 9B, 9C).

Figure 11A:
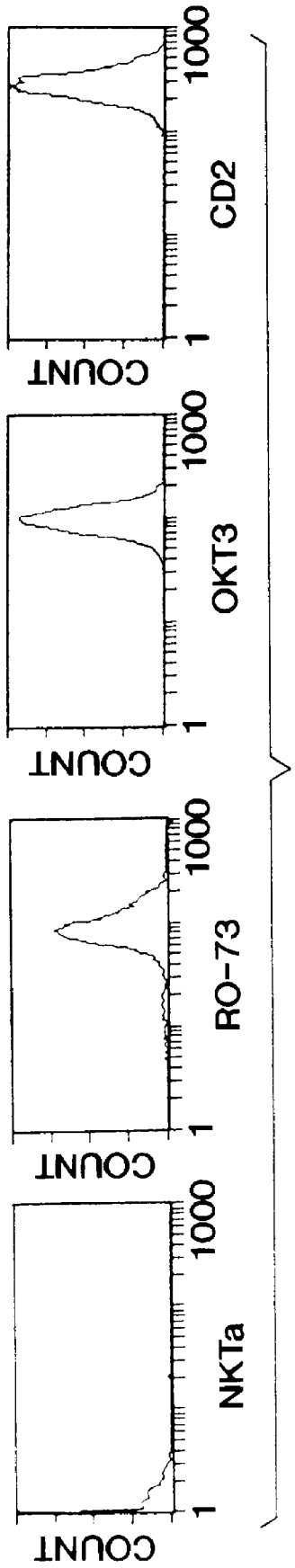
Figure 11B:
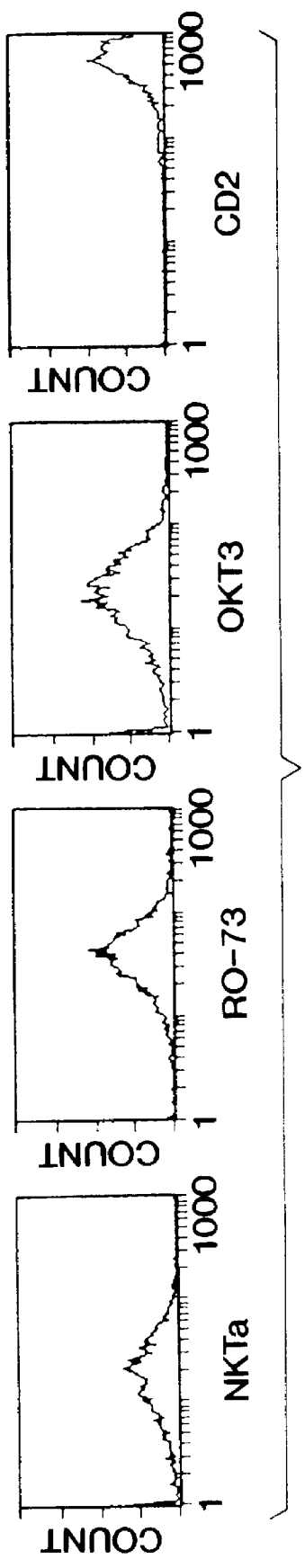

FIGS. 11 (A–B) represents the analysis by cytofluorimetry of the comodulation with the CD3 molecule of the TCR structure of clone 3025 recognized by the monoclonal antibody RO-73 respectively in the absence (FIG. 11A) or in the presence of anti-CD3 antibodies (FIG. 11B).

The comodulation-control is given with the monoclonal antibodies NKTa, OKT3 and anti-CD2 respectively.

Figure 12A:
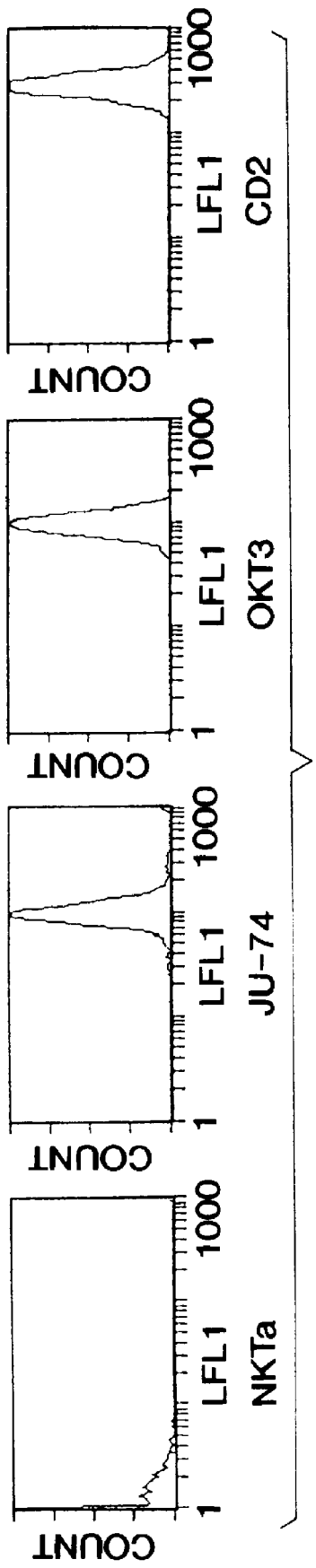
Figure 12B:
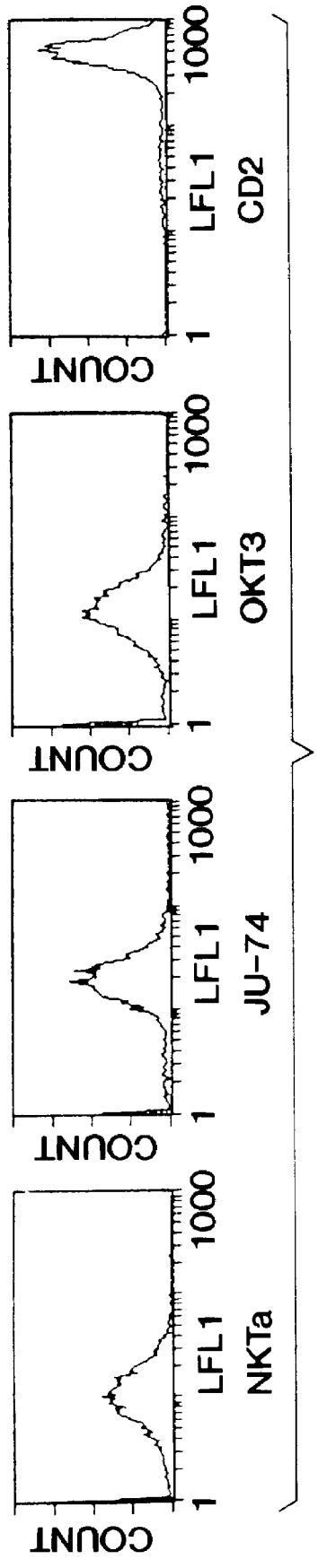

FIGS. 12 (A–B) represent the analysis by cytofluorimetry of the comodulation with the CD3 molecule of the TCR structure of clone 3025 recognized by the monoclonal antibody JU-73, respectively in the absence (FIG. 12A) or in the presence of anti-CD3 antibody (FIG. 12B).

Figure 13A:
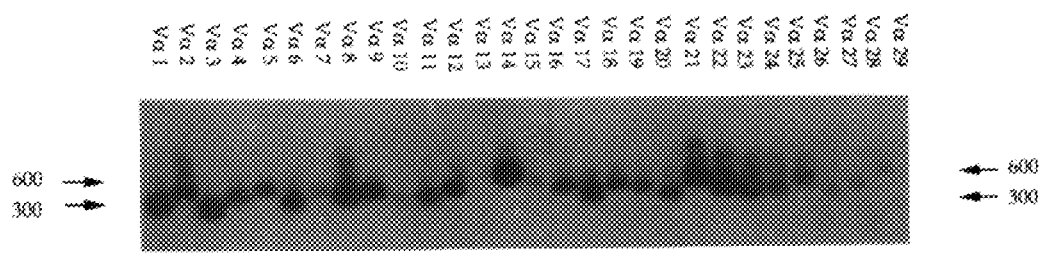
Figure 13B:
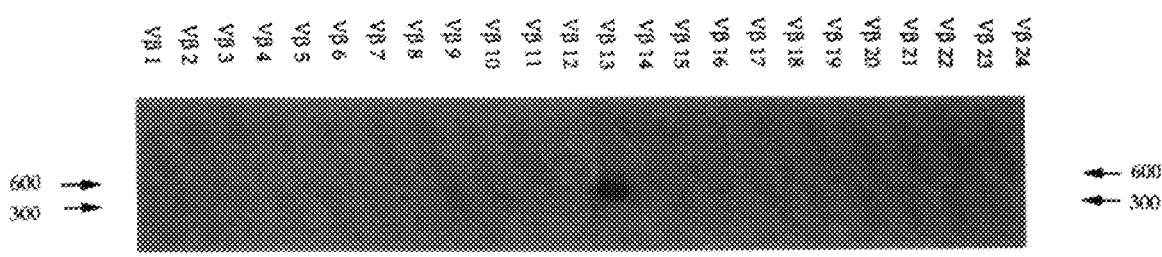

FIG. 13 (A–B) represent the detection by autoradiography of amplified transcripts of TCR α chains (FIG. 13A) and β chains (FIG. 13B) expressed by the RO-73$^+$cells.

I—Obtaining the cDNA and amplification by PCR

The peripheral lymphocytes of an individual are used as the DNA source. The total RNA was prepared according to the method using guanidinium isothiocyanate and caesium chloride (Chirgwin (12)) or according to a one-stage method by extraction with guanidinium isothiocyanate, phenol and chloroform (Chomcyznski (13)).

The first cDNA strand was synthesized in a final volume of 50 microlitres at a temperature of 42° C. for 1 hour using 5 micrograms of total RNA, reverse transcriptase and a primer A which is specific to the Cβ region constituted by the sequence 5'-TATCTGGAGTCATTGAGGGCGGGC (SEQ ID No. 20). This material was then purified by extraction with phenol/chloroform and precipitation with ammonium acetate. After selecting a $^{0.45}/_1$ kb fraction on agarose gel, the addition of a dG end is carried out on the RNA/cDNA hetero complex in a $CoCl_2$ addition buffer with 14 units of terminal deoxynucleotidyl transferase (TdT) for 30 minutes at 37° C. The reaction was stopped by maintenance at 70° C. for 10 minutes. 1N NaOH (⅓ volume) was added and the sample was incubated at 50° C. for 1 hour to hydrolyze the RNA, then neutralized with Tris HCl 2M pH 8 and 1N HCl. After extraction with a phenol/chloroform mixture the first cDNA strand at end G was precipitated with ethanol and subjected to an amplification using the PCR technique (Polymerase Chain Reaction described by Saiki et al. (14)) in a final-volume of 100 microlitres containing 50 mM of KCl, 10 mM of Tris-Cl pH 8.3, 1.5 mM of $MgCl_2$, 0.1% (weight/volume) of gelatine, 200 micromoles of dNTP, 2.5 units of Taq polymerase and 100 picomoles of two primers. The two primers used are, on the one hand a poly-C primer (5'-GCATGCGCGCGGCCGCGGAGG-14C) (SEQ ID No. 21) described by Loh et al. (15) as well as a primer B specific to the Cβ region (5'-TGTGGCCAGGCATGCCAGTGTGGCC) (SEQ ID No. 22).

25 amplification cycles are carried out followed by a final 15 minute elongation period at 72° C. Each cycle includes a denaturation stage at 92° C. for 1 minute, a hybridization stage at 55° C. for 2 minutes and an elongation period at 72° C. for 4 minutes. The amplified products are then precipitated with ethanol, resuspended in 30 mM of sodium acetate pH 5, 50 mM NaCl, 1 mM $ZnCl_2$, glycerol 5% by volume and $^1/_{10}$ of this material is purified as a function of size on a 1% low melting point agarose gel.

A second amplification phase is then carried out directly on approximately 10% of the band containing the agarose following the same conditions as previously, except that the primer 5'-GGTGTGGGAGAATTCTGCTTCTGA (SEQ ID No. 23) is used as primer C which is specific to the Cβ region. The reaction mixture is then precipitated with ethanol and resuspended in 60 $\mu$l of $H_2O$.

II—Cloning and sequencing of cDNAs

⅓ of the product of the second amplification is digested with Sac II, separated on 1% agarose gel and purified by absorption on glass beads. The material is inserted in the Bluescript SK$^+$ vector (Stratagene, La Jolla, U.S.A.) and the recombinants obtained are used to transform the XL1-blue strains of *E. Coli* (Stratagene). After sedimentation in the presence of X-gal and IPTG, a test is carried out on the white colonies using a "dot blot" technique and a third oligonucleotide specific to the Cβ region (5'-TCTGCTTCTGATGGCTCAA) (SEQ ID No. 24) labelled with $^{32}p$ is used as a probe. The plasmid DNA of positive colonies is extracted and sequencing takes place under the two strands by the process of termination of the dideoxy chain (Sanger et al. (16)) with Sequenase 2.0 (United States Biochemicals, Cleveland, U.S.A.) following the supplier's recommendations.

The sequences obtained were compared with published Vβ sequences using the method developed by Lipman and Pearson (17). The presumed start codons were identified by searching for the presence of the Kozak consensus sequence for the initiation sites of translations in the eukaryotic cells (Kozak (18)). The presence of hydrophobic leader sequences of the N-terminal side was detected by analysis of the hydrophobicity according to the method described by Kyte (19).

III—Southern blot analysis

The DNA was extracted from the human erythroleukaemic cell line K562 and digested with one of the following restriction enzymes: Eco RI, BamH I or Hind III. The DNA (15 micrograms) was subjected to electrophoresis on 0.7% agarose and transferred onto Nylon membranes as described by Triebel et al. (20). The hybridizations were carried out at 65° C. with 6×SSC, 0.5% of SDS, 5×Denhardt's and 100 micrograms of denatured salmon sperm DNA for 16 hours. The membranes were washed at 65° C. with 2×SSC, 0.2% of SDS.

As Vβ specific probes, are used the probes obtained by amplification of V-J-C cDNA using as a primer the poly-C primer and the C primer. The probes were purified on 1% agarose gel. DNA probes labelled with $^{32}p$ were prepared from fragments purified on agarose by the Feinberg method (21).

IV—Results

By using the A-PCR method, 350 cDNA which hybridize with the Cβ clone were cloned, then sequenced. Among these, 226 cDNA correspond to the V-J-Cβ variable regions only.

The Vβ sequences of the invention are shown in the list of sequences under SEQ ID No. 2 to 19. The sequences SEQ ID No. 3 to 5 correspond to three new sub-families while the sequences SEQ ID No. 2 and 6 to 19 correspond to new members of Vβ sub-families or to extensions of known Vβ segments.

Vβ w21 sub-family (SEQ ID No. 2)

This sub-family has been identified by the clone IGR b02 (SEQ ID No. 2).

This sequence shows for the coding part a similarity of about 85% with the sequence HSTCRB23 (Wilson et al. (41)).

Vβ w22 sub-family (SEQ ID No. 3)

The segment SEQ ID No. 3 has been defined as a consensus sequence from 23 distinct clones of cDNA. A C instead of a T is observed in position 322 and an A instead of a G is observed in position 350.

Vβ w23 sub-family (SEQ ID No. 4)

Figure 1:
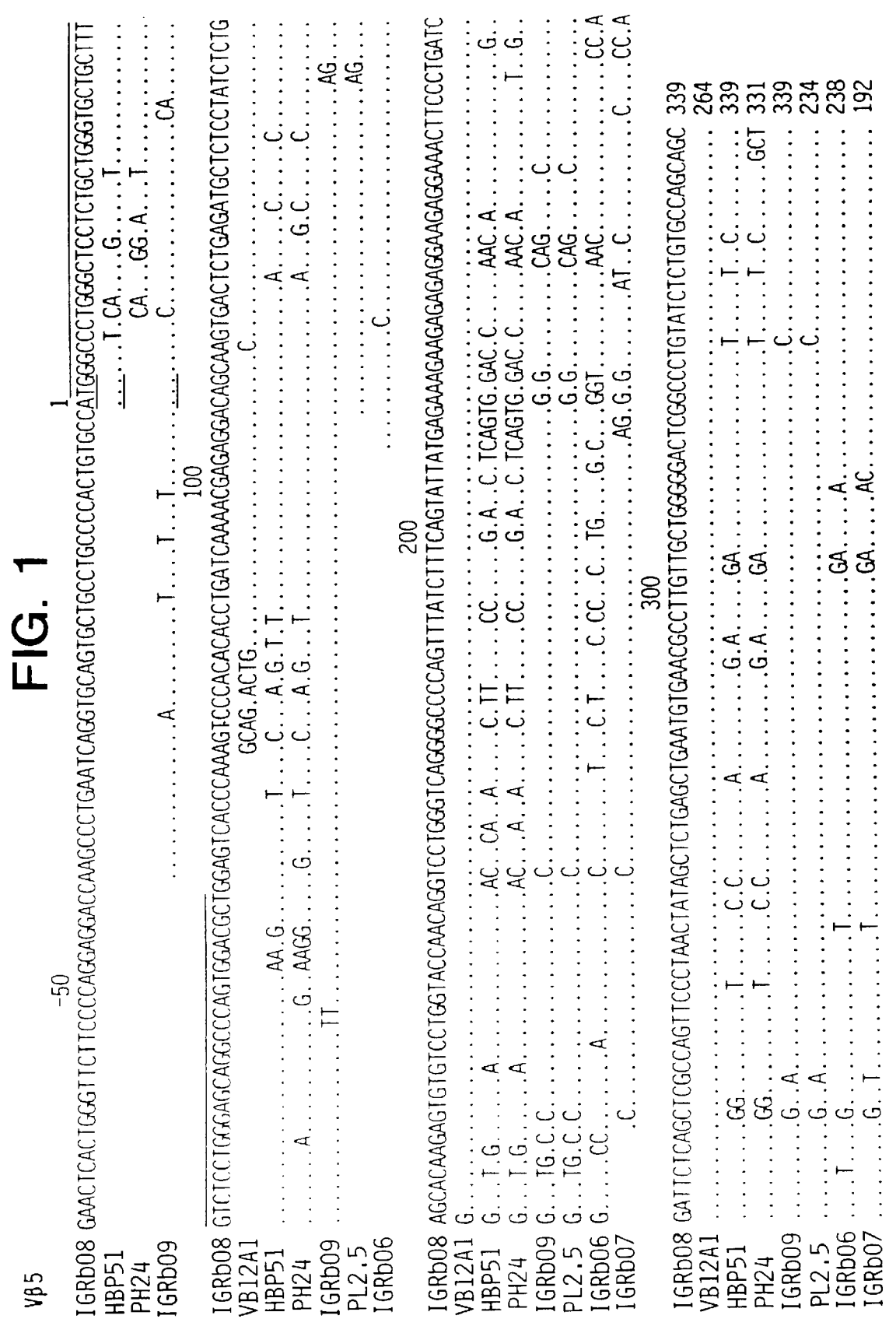

The segment ID No. 4 has been defined as a consensus sequence from 4 distinct clones. A G instead of an A is observed in position 154 and an A instead of a G is observed in position 160. It shows a similarity of 75.7% with the sequence VB12A1 (Leiden already quoted) but shows a similarity of less than 75% with the other members of the Vβ 5 sub-family (represented in FIG. 1) Therefore it is not part of the V 5 sub-family.

Vβ w24 subfamily (SEQ ID No. 5)

The segment SEQ ID No. 5 has been defined from 2 distinct clones of cDNA.

Figure 7:
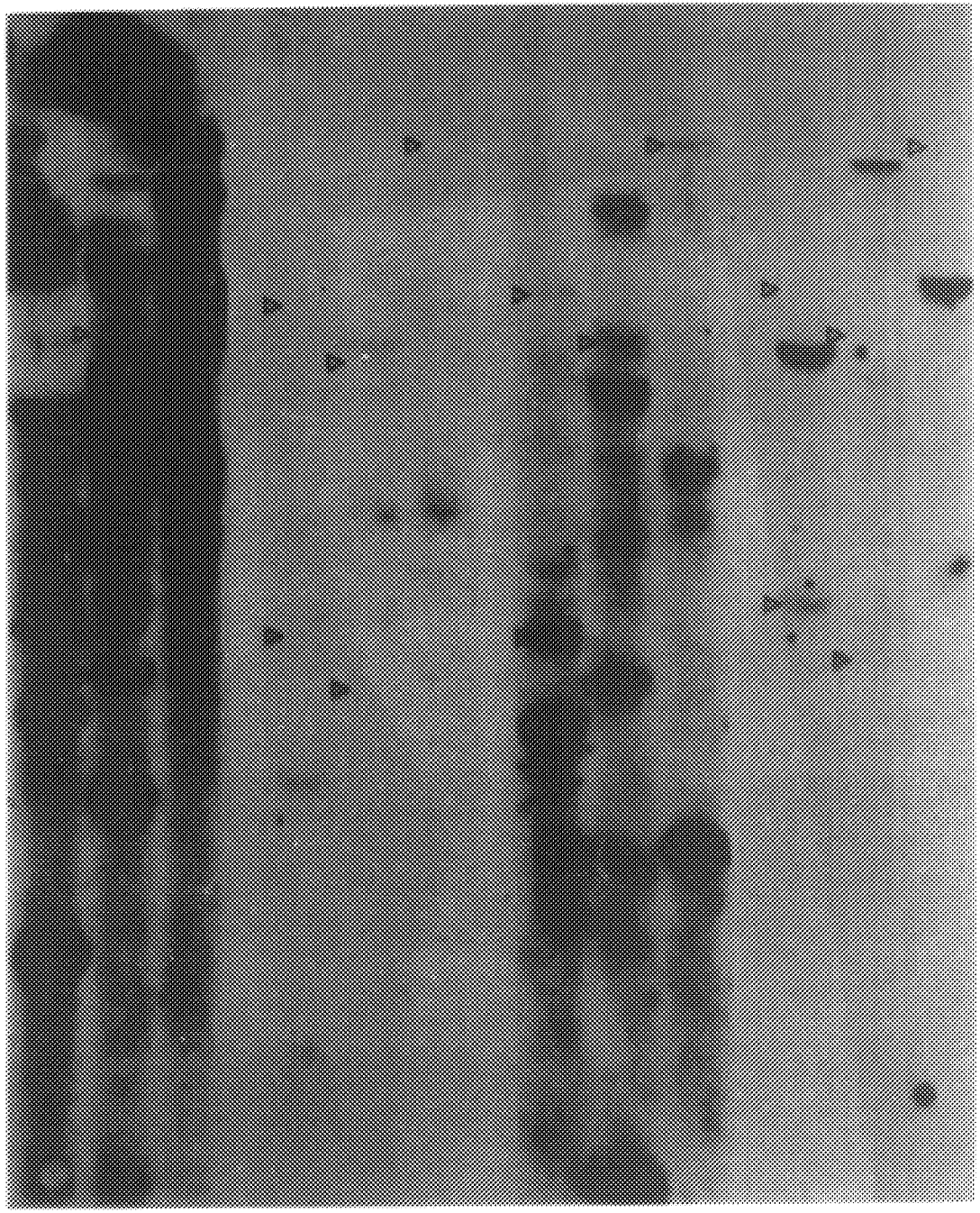

The Southern blot analyses of germinal line DNA subjected to digestion by endonucleases, using V-J-Cβ probes containing Vβ fragments corresponding to the Vβ w21 to Vβ w24 sub-families were carried out in "low stringency" hybridization conditions to identify the number of Vβ genetic segments belonging to each family and to characterize the DNA restriction fragments carrying these Vβ genetic segments. The representative results are shown in FIG. 7.

These analyses are compatible with the presence in the K 562 erythroleucemic cells of at least three genetic segments for the Vβ w21 sub-family, two for the Vβ w23 sub-family and one for the Vβ w22 and Vβ w24 sub-families.

The sizes of the germinal DNA restriction fragments are as follows:

Vβ w21: EcoR I 1.7-,3- and 6.5 kb, Hind III 2.5-, 7.2-, 11.7-, 14- and 18 kb, BamH I 5.5-, 16.5- and 23 kb;

Vβ w22: EcoR I 2.8 kb, Hind III 8.8 kb, BamH I 5.3 kb;

Vβ w23: EcoR I 3.2- and 4.4 kb, Hind III 7.4-, 15.5- and 16.5 kb, BamH I 2.5- and 5.7 kb;

Vβ w24: EcoR I 8 kb, Hind III 20 kb and 7.3 kb, BamH I 11,- and 22 kb.

Vβ 5 sub-family (FIG. 1):

SEQ ID No. 6 and 7 (IGR b06 and IGR b07)

These sequences show a similarity of 79 to 86% and 76 to 70% respectively with the 4 previously known segments VB12A1 (Leiden already quoted), HBP51 (Kimura (23)), PH24 (Tillinghast already quoted) and PL25 (Concannon (24)) and represent new members.

SEQ ID No. 8 and 9 (IGR b08 and IGR b09)

These sequences correspond to extensions of the 5' side of VB12A1 and PL25 clones respectively. For SEQ ID No. 8 two nucleotide substitutions are observed relative to VB12A1.

Figure 2A:
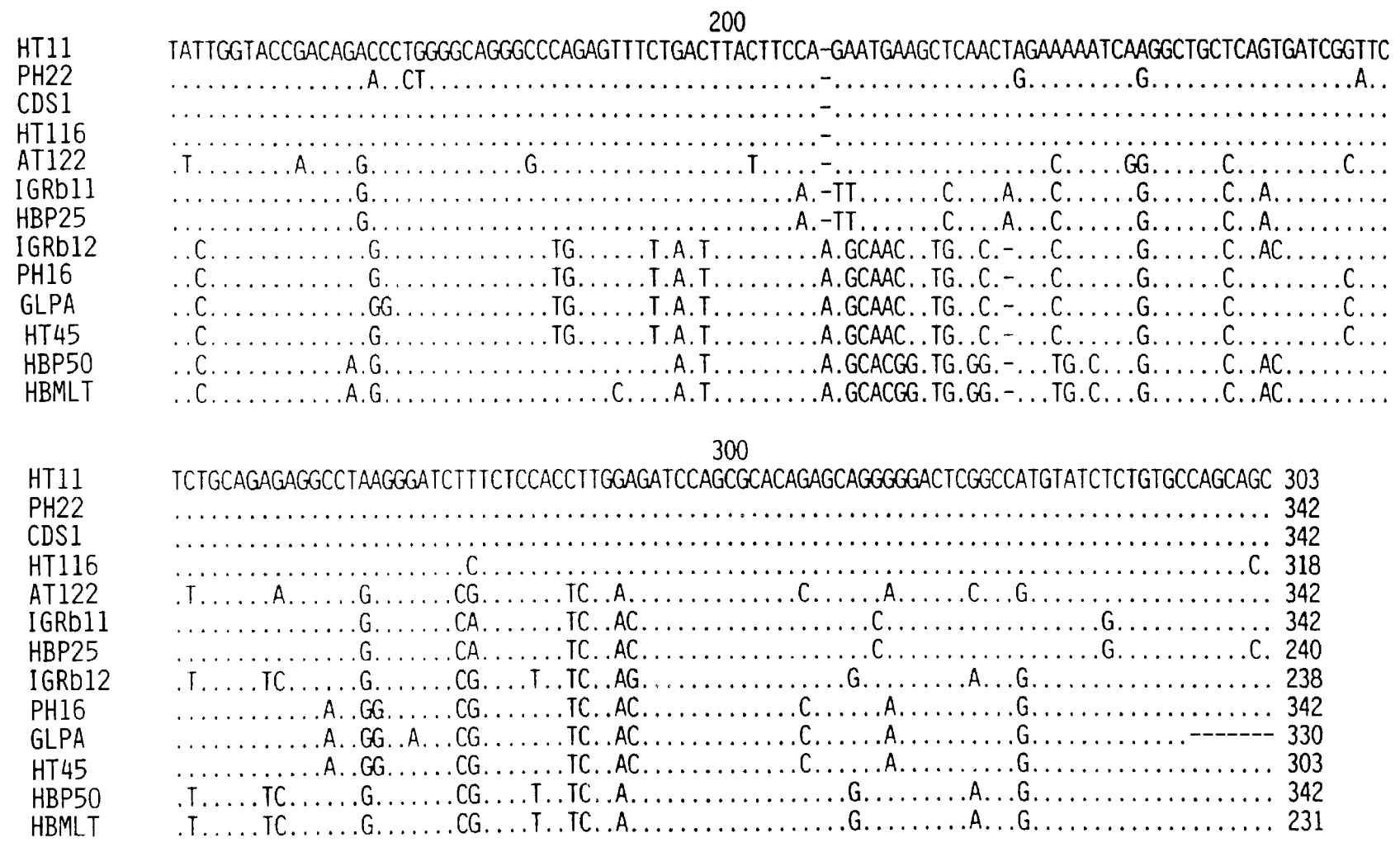

Vβ 6 sub-family (FIG. 2):

SEQ ID No. 10 (IGR b11)

This sequence corresponds to an extension of the 5' side of clone HBP25 (Kimura, already quoted).

SEQ ID No. 11 (IGR b12)

This sequence which represents a new member shows a similarity of nucleotides of 94% with PH 16 (Tillinghast already quoted), GPPA (Li, already quoted) and HT45 (Kimura (25)).

Vβ 12 sub-family (FIG. 3):

SEQ ID No. 12 (IGR b13)

This sequence which represents a new member shows a similarity of greater than 85% with the sequences PH27 (Tillinghast already quoted), and PL42 (Concannon, already quoted).

Vβ 13 sub-family (FIG. 4):

SEQ ID No. 13, 14 and 15 (IGR b14, IGR b15 and IGR b16)

The sequences SEQ ID No. 13 and 14 which represent new members show a similarity of 78 to 91% and 77 to 79% respectively with the other known sequences HBVP34 (Kimura (23)) and CEM (Duby (26)).

The sequence SEQ ID No. 15 show a similarity of 94% with HBVP34. It should be noted that the sequence SEQ ID No. 15 shows an intron (represented by lower case characters) in the leader region. The sequence SEQ ID No. 15 is a consensus sequence. A C instead of a T is observed in position 231 and an A instead of a G is observed in position 259.

Figure 5:
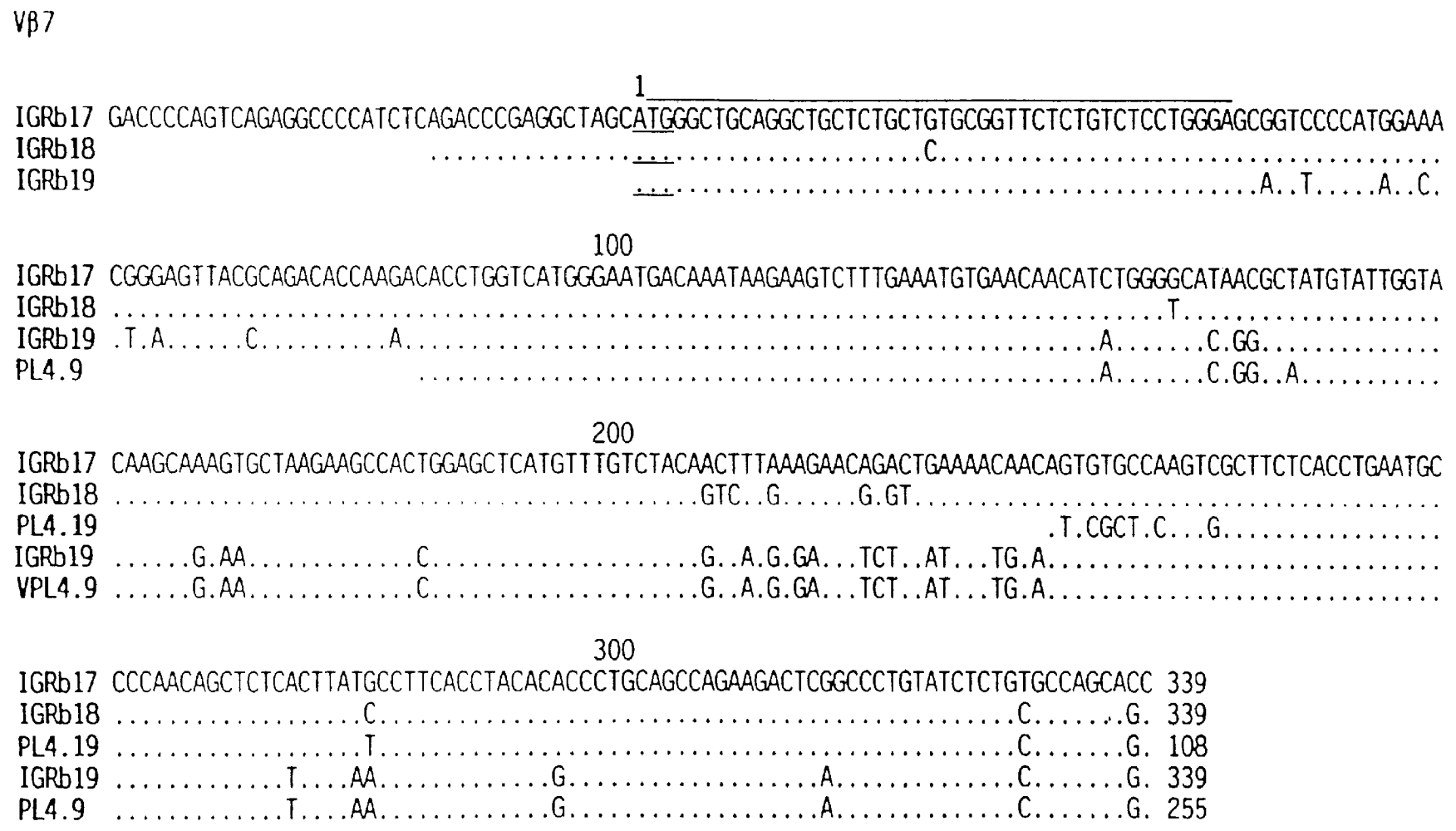

Vβ 7 sub-family (FIG. 5):

SEQ ID No. 16 and 17 (IGR b17 and IGR b18)

These sequences show a strong similarity with the truncated sequence PL4.19 (Concannon, already quoted) and the extension of the 5' side up to the start signal of the translation.

SEQ ID No. 18 (IGR b19)

This sequence extends the sequence PL4.9 (Concannon already quoted) of the 5' side up to the start signal of the translation.

Vβ 9 sub-family (FIG. 6):

SEQ ID No. 19 (IGR b20)

This sequence extends the sequence PL2.6 (Concannon, already quoted) of the 5' side. A difference between the two sequences is observed in positions 98 and 100 corresponding to different amino acids.

The present invention also aims at providing specific oligonucleotides of different Vβ sub-families, which ca be used as primers for the amplification of DNA corresponding to these different Vβ sub-families, with a view, for example, of a study of the expression of certain Vβ sub-families in a patient and finally of a diagnosis of immune disorders, as indicated above.

The predominant expression of certain Vβ sub-families has already been studied using an incomplete range of oligonucleotides.

In this way Sottini et al. (33) have shown, using a range of oligonucleotides, a predominant expression of certain Vβ's in patients suffering from rheumatoid arthritis.

Similarly, Choi Y. et al. (32) have shown, using a range of oligonucleotides, the stimulation of T lymphocytes by Staphylococcus aureus toxins by the intermediary of specific Vβ's.

The present invention aims to provide a complete range of oligonucleotides allowing the study, of both known Vβ sub-families and new Vβ sub-families of the invention and which are completely specific to each sub-family. Thus the oligonucleotides have been chosen and synthesized to this end and to the requirements of modifications of one or two nucleotides which have been introduced relative to the natural sequences to reduce the cross-reactions between sub-families.

Thus a subject of the present invention is also oligonucleotides which can be used as primers for the amplification of DNA corresponding to the variable regions of chains of T-cell receptors, chosen form the sequences SEQ ID No. 25 to 48.

Also a subject of the present invention is the use, as primers for the amplification of DNA corresponding to the variable regions of chains of T-cell receptors, of oligonucleotides chosen from the sequences SEQ ID No. 25 to 48.

Also a subject of the present invention is a detection process of nucleotides sequences coding for the V segments of T receptors or of cDNA corresponding to transcription products of the latter, in a biological sample, characterized in that it includes:

a) the amplification of DNA with at least one pair of primers formed by one of the oligonucleotides defined above and one oligonucleotide belonging to a Cβ segment, and b) the detection of amplified sequences with a Cβ probe.

The oligonucleotide belonging to a Cβ segment used for the amplification can be, in particular, chosen from the sequences SEQ ID No. 49 and 50.

To check the efficiency of the amplification, the operation is preferably carried out in the presence of a pair of control primers and the corresponding control sequence amplified using a corresponding control probe is detected.

This pair of control primers can correspond to two Cβ segments, for example the CαE and CαJ primers corresponding to sequences SEQ ID No. 55 and 56. A Cα detection probe (corresponding for example to the sequence SEQ ID NO. 57) is then used. But this pair of primers is advantageously constituted by two primers belonging to β-actin, notably those corresponding to sequences SEQ ID No. 52 and 53. Then a detection probe corresponding to a sequence of β-actin, such as the sequence SEQ ID No. 54, is used.

Also a subject of the present invention is a diagnostic kit for the implementation of the process defined previously, which includes:

a) at least one oligonucleotide chosen from the sequences SEQ ID No. 25 to 48, b) a Cβ primer, c) a Cβ probe.

In addition such a kit advantageously contains:

d) a pair of control primers, e) a control probe.

This kit can contain in particular:

a) the group of 24 oligonucleotides corresponding to sequences SEQ ID No. 25 to 48, b) a Cβ primer chosen from the sequences corresponding to sequences SEQ ID No. 49 and 50, c) a pair of control primers for β-actin having a sequence corresponding to sequences SEQ ID No. 52 and 53 respectively, d) a Cβ probe corresponding to the sequence SEQ ID No. 51, e) a control probe for β-actin corresponding to the sequence SEQ ID No. 54.

In the information given in the list of sequences for the sequences 25 to 54, the sequences SEQ ID No. 25 to 45 correspond to sequences belonging to clones of known Vβ1 to Vβ20 sub-families (available from the EMBL database) or to sequences which differ from them by one or two nucleotides. The sequences SEQ ID No. 45, 46, 47 and 48 correspond to sequences belonging to clones of new sub-families of the invention, corresponding to sub-families provisionally designated Vβ w21, Vβ w22, Vβ w23 and Vβ w24 (w indicating that the designation is pending definitive designation).

The sequences SEQ ID No. 49 and 50 are two examples of Cβ oligonucleotides which can be used as primers for amplification.

The sequence SEQ ID No. 51 is the sequence of a Cβ probe which can be used for the detection of amplified DNAs.

Finally, the sequences SEQ ID No. 52, 53 and 54 are respectively the sequences of a pair of oligonucleotides belonging to the sequence of β-actin which can be used to check the amplification and the sequence of a probe for detecting the corresponding amplified DNAS.

In the list of sequences the position indicated is the position of the 5' end counting from the predicted initiation site of the ATG translation. In the case where the sequences are incomplete (unknown 5' region), the position (marked with an asterisk) is given relative to the first nucleotide of the sequence. The underlined nucleotides correspond to mismatches introduced relative to the natural sequence.

The oligonucleotides were sythesized with an Applied Biosystems 381 A automated DNA synthesizer using the β-cyano-ethylphosphoramidite method (Sinha N. et al. (34)) and following the protocol recommended by the manufacturer. The oligonucleotides were detritylated in the apparatus, cleaved form the support and deprotected with ammonia (at 60° C. for 5 hours). The crude products were purified by inverted phase high pressure chromatography on a $\mu$-bondapak C18 column using an acetonitrile gradient (9 to 15%) in a 0.01 M triethylammonum acetate buffer at pH 5.5.

The amplification carried out using the primers according to the invention can be, in particular, the technique of amplification by PCR (Polymerase Chain Reaction) as described by Saiki et al. (14) and in U.S. Pat. Nos. 4,683, 195, 4,683,202, 4,889,818.

For the PCR, a double strand DNA can be used which is denatured or a cDNA obtained from RNA using reverse transcriptase as mentioned above.

The polymerization agent is a DNA polymerase, in particular, Taq polymerase.

Generally the amplification cycle is repeated 25 to 40 times.

The probes which are used for detecting the amplified sequences can be obtained by labelling the oligonucleotides with a radio-active isotope, which leads to detection by autoradiography, or by conjugation with an enzyme such as peroxidase (ECL Amersham system), alkaline phosphatase or β-galactosidase (Tropix Ozyme system), which leads to detection by chemiluminescence.

The following example illustrates the implementation of the detection process according to the invention.

The peripheral lymphocytes of a healthy individual were prepared by density gradient centrifugation. The total DNA was extracted according to a one-stage method by extraction with guanidium isothiocyanate, phenol and chloroform (Chomczynski, 13). The complementary DNA was synthesized in a final volume of 20 μl at 42° C. for one hour using 1 to 5 μg of total RNA, the reverse transcriptase and the CβB primer (1.25 uM).

The material obtained was then heated at 95° C. for 3 minutes before being subjected to an amplification according to the PCR technique using in parallel each of the specific Vβ primers corresponding to sequences SEQ ID No. 25 to 48 and the Cβ B primer specific to the Cβ region (SEQ ID No. 50). This amplification was carried out in a final volume of 10 μl per tube containing 50 mM of KCl, 10 mM of tris-HCl pH 8.3, 1.5 mM of $MgCl_2$, 0.1% (weight/volume) of gelatine, 200 μM of dNTP, 0.25 units of Taq polymerase and 0.25 μM of each primer. A control amplification was carried out in each tube from 25 mN of a DNA fragment of β-actin of 877 base pairs prepared by PCR and Act 1 and Act 2 primers (SEQ ID No. 52 and 53) specific to actin. 30 amplification cycles were carried out followed by a final elongation stage of 5 minutes at 72° C. Each cycle included a denaturation stage at 94° C. for one minute, a hybridization stage at 65° C. for one minute and an elongation period at 72° C. for one minute.

The products obtained were separated by electrophoresis on 2% agarose gel, transferred onto nylon membranes in an alkaline buffer and hybridized simultaneously with the Cβ C oligonucleotide probes (SEQ ID No. 51) and Act 3 (SEQ ID No. 54) labelled with $^{32}p$ by the polynucleotidyl T4 kinase enzyme. The hybridization was carried out at 42° C. for 16 hours in a buffer containing 6×SSC, 0.5% SDS, 5×Denhardt's, 0.05% $NaH_2PO_4$ and 100 μg/ml of denatured salmon sperm DNA. The membranes were then washed with SSC 6×, 20 mM $NaH_2PO_4$, twice at ambient temperature for 5 minutes and once at 50° C. for 30 minutes then autoradiographed.

Figure 8:
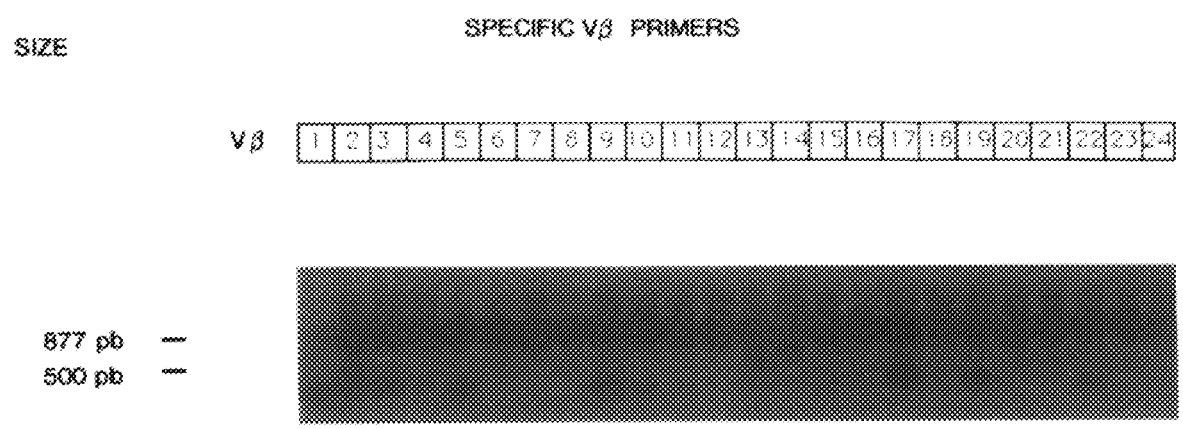
FIG. 8 represents the detection by autoradiography of amplified transcripts of TCR β chains expressed by the peripheral lymphocytes of a healthy individual and of a co-amplified β-actin control.

The results obtained are shown in FIG. 8.

The actin control (band of 877 base pairs) allows the amplification to be verified in all wells. A specific signal appears below this band the size of which corresponds to the size of corresponding amplified fragments, each fragment having a length corresponding to the distance between the locus of the specific Vβ oligonucleotide and the Cβ primer.

With the individual tested, FIG. 8 shows the preferential expression of certain genetic segments defined relative to the others. For example, the Vβ1 and 2 sub-families are more represented than the other sub-families.

EXAMPLE OF THE PREPARATION OF ANTI Vβ13 MONOCLONAL ANTIBODIES

RO-73 AND JU-74 MONOCLONAL ANTIBODIES

1) Immunizing cells

The clone T 3025 (Moebius et al. (35)) was cultivated in complete medium containing DMEM (Seromed), 8% AB human serum, IL-2 and TCGF as described by Hercend et al. (36). Periodic restimulations were carried out on allogenic cells in the presence of IL-2. The messenger RNAs coding for the T receptor expressed by these cells were sequenced using the A-PCR technique and represent rearrangements of genetic segments Vα10 (sequence HAP58, Yoshikai et al. (37)) and Vβ13 (sequence IGRb16=SEQ ID No. 15 indicated above).

2) Immunization of mice 6-week old Biozzi mice (Curie Institute, Paris, France) were immunized with whole T cells of clone 3025. After a first intraperitoneal injection of $5×10^6$ cells in Freund's complete adjuvant, the mice received three intraperitoneal injections of $5×10^6$ cells in Freund's incomplete adjuvant at three-week intervals. Two weeks after the last intraperitoneal injection the mice received an intravenous injection of $2×10^6$ viable cells. The mice were killed three 35 days later and the spleen was removed.

3) Fusion

The fusion of spleen cells with the myeloma which does not secrete NS-1 was carried out according to the Kohler and Milstein method (38). The NS-1 cells (Kohler and Milstein (39)) were cultivated in a medium containing DMEM (Seromed), 8-azaguanine (Sigma, Saint Louis, Mich.), 10% horse serum (Seromed, lot No. 5Z04), penicillin and streptomycin (Eurobio), glutamine (Seromed, 200 mM) and sodium pyruvate (Gibco, 100 mM).

The splenocytes were fused with NS-1 cells with polyethylene-glycol (PEG 1000, Merck) in a ratio of 4 spleen cells per one myeloma cell. After the fusion, the cells were cultivated at $3×10^6$ cells per ml in plates of 96 wells (Nunc) in a HAT selection medium containing DMEM, 10% horse serum, 10% foetal calf serum (Seromed, lot No. 219195), aminopterin (Gibco), hypoxanthine and thymidine (Gibco), penicillin and streptomycin, glutamine, sodium pyruvate and NCTC 109 (Eurobio). Fresh medium was added to the wells 2 days (50 μl per well) and 9 days (100 μl per well) after fusion. The culture was carried out at 37° C., in an incubator containing 10% $CO_2$.

4) Screening of hybridomas

The supernatant of hybridomas obtained was collected 15 days after fusion and its reactivity was tested with the immunizing cell by indirect immunofluorescence and analysed by flow cytometry analysis. In brief, the T3025 cells were incubated at 4° C. for 30 minutes with the hybridoma supernatant (100 μl per 300,000 cells), washed and labelled with a mouse anti-immunoglobulin goat antibody conjugated with fluorescein (Coulter Electronics, Hialeah, Fla.). The cells were then analyzed by flow cytometry analysis. (Coulter Profile). As is shown in FIGS. 9A and 10A, the supernatants of hybridomas RO-73 and JU-74 allow the labelling of 100% of the cells of immunizing clone 3025. An anti-CD3 antibody (OKT3 Ortho-Co) and the anti-clonotype NKTa antibody (IgG1, Hercend et al (40)) served respectively as positive and negative controls in this experiment.

The anti-T receptor specificity of the monoclonal antibodies was analyzed according to the following criteria:

1—the antibodies must recognize the immunizing T clone 3025 but not a T clone carrying a different T-cell receptor (TCR), for example the clone 12410 (Moebius et al., (35)) expressed TCR: Vα3/Vα17).

2—The antibodies must react with a low percentage of circulating lymphocytes (PBL).

3—The structure of the surface recognized by the antibodies on the immunizing cell must co-modulate with the CD3 molecule at the time of the incubation of the cells in the presence of anti-CD3 antibodies (Meuer et al. (1)).

As FIGS. 9 and 10 show, the supernatants of hybridomas RO-73 and JU-74 react with 100% of the cells of immunising clone 3025 (FIG. 9A and 10A), less than 2% of the cells of clone 12410 (FIG. 9B and 10A) and 1 to 3% of the PBLs (FIG. 9C and 10C).

For the co-modulation experiments, the cells of clone 3025 ($10^6$ cells per ml) were incubated in medium only or in the presence of anti-CD3 antibodies (OKT3) in 24-well culture plates. After incubation for 24 hours the cells were collected and labelled with the supernatant of hybridoma RO-73 or JU-74, anti-CD3 monoclonal antibody or an anti-CD2 control monoclonal antibody (Coultronics Co.) then analyzed by flow cytometry analysis. As FIGS. 11 and 12 show, the flow cytometry analysis of cells incubated in the presence of anti-CD3 monoclonal antibody (FIG. 11B and 12B) shows a diminution of the fluorescence intensity for the anti-CD3 monoclonal antibody as well as for RO-73 and JU-74, while the labelling intensity with anti-CD2 monoclonal antibody increases in comparison to the intensity obtained respectively in the absence of anti-CD3 antibody (FIG. 11A and FIG. 11B). These results indicate that the molecule recognized by the RO-73 and JU-74 antibodies co-modulates with the CD3 molecule at the surface of the cells of clone T 3025.

6) Isolation of a sub-clone

The cells of the initial hybridomas, respectively RO-73 and JU-74 were distributed on culture plates at the rate of 0.5 cell per well in complete HAT medium, on irradiated syngenic spleen cells. Three sub-clones were selected for each of the hybridomas RO-73 and JU-74. These cells produce monoclonal antibodies whose reactivity is identical to that of the initial hybridomas (results not shown).

The sub-clones were cultivated in non-selective medium containing DMEM, 10% foetal calf serum, 10% horse serum, hypoxanthine, thymidine, penicillin and streptomycin, glutamine, sodium pyruvate and NCTC 109.

The cells of the hybridomas or sub-clones were frozen in foetal calf serum containing 10% of dimethyl sulphoxide (DMSO, Merck) and stored in liquid nitrogen.

7) Isotyping of monoclonal antibodies

The isotypes were determined by immunodiffusion on a solid support using an "INNO-LIA mouse mAb isotyping" kit (Innogenetics) for the determination of the isotypes of immunoglobulins in the supernatants of the culture. RO-73 and JU-74 are mouse immunoglobulins of isotype IgG1, kappa.

8) Purification of monoclonal antibodies

Ascites were produced in nude mice. The ascitic liquid obtained was filtered through cotton to eliminate the fibrin and precipitated with sodium sulphate (18%). The deposit obtained was suspended in PBS buffer, ⅓ diluted in a buffer (NaCl 4.5 M, Glycine 2.25 M, pH 8.8) and loaded into a column of Protein A-Sepharose 4 Fast Flow equilibrated in the loading buffer (NaCl 3 M, glycine 1.5 M, pH 8.8). A major peak of immunoglobulins was eluted at pH 6 using successive elution buffers of decreasing pH. This major peak was purified on an ion exchange column (Q Sepharose Fast Flow) in a Tris 50 mM, pH 8 buffer and eluted with an NaCl gradient.

The purity of the preparation was verified by electrophoresis in a PHAST system (Pharmacia LKB, Uppsala, Sweden) and the purified immunoglobulins were tested by indirect immuno-fluorescence on the cell 3025, as indicated previously.

As an example, for 30 ml of ascite of the hybridoma RO-73, 32 mg of purified immunoglobulins was obtained after purification on Protein A and Q Sepharose Fast Flow.

9) Percentage of PBL recognized by the monoclonal antibodies

The percentage of circulating lymphocytes recognized respectively by the monoclonal antibodies RO-73 and JU-74 was determined for 10 different healthy donors. The results are shown in Table 1. The monoclonal antibody JU-74 recognizes less than 0.5% to 2.1% of the PBLs (average 1.08%) and the monoclonal antibody RO-73 recognizes from 0.5% to 2.2% of the PBLs according to the individuals (average 1.09%). For a given individual, the monoclonal antibodies RO-73 and JU-74 recognize respectively approximately the same percentages of circulating lymphocytes.

TABLE 1

Reactivity of monoclonal antibodies RO-73 and JU-74 with peripheral blood cells

| Donor | RO-73 | JU-74 |
| --- | --- | --- |
| BQ | 2,2 | 2,1 |
| BY | 0,9 | 1,1 |
| BZ | <0,5 | <0,5 |
| CA | 0,5 | <0,5 |
| CB | 0,5 | 0,6 |
| CD | 1,8 | 1,7 |
| CE | 0,4 | 0,3 |
| CH | 1,6 | 1,3 |
| CI | 1,4 | 1,2 |
| CJ | 1,1 | 1,5 |

10) Purification of PBLs recognized by the monoclonal antibodies

The PBLs recognized respectively by the monoclonal antibodies RO-73 and JU-74 were purified from a normal donor using a positive selection process with magnetic beads (Dynabeads, Dynal). In brief, 1 to $4 \times 10^9$ PBL were labelled by one or other of the above purified monoclonal antibodies and incubated with ready-to-use Dynabeads M-450 beads covered with a mouse anti-IgG goat serum, in the proportion of 3 beads per labelled cell. The positive cells were then separated using a magnet. After several washings, the cells were incubated with an excess of mouse anti-IgG goat immunoglobulins ("Detach-a-beads", Dynatech) in order to detach the magnetic beads then directly analyzed by flux cytometry analysis after labelling with the monoclonal antibody RO-73 or the monoclonal antibody JU-74, respectively.

The selected positive cells were cultivated in a microplate in the presence of IL-2 on the irradiated allogenic cells then purified again with magnetic beads after culturing for about a week in order to obtain a preparation with a purity greater than 95%.

For the monoclonal antibody JU-74, $8 \times 10^6$ positive cells of 96% purity were obtained, after a one-week culture, from $1 \times 10^9$ PBL from a healthy donor containing initially 1.7% of JU-74+ cells.

For the monoclonal antibody RO-73, $9 \times 10^6$ positive cells of 98% purity were obtained, after a 10-day culture, from $1.2 \times 10^9$ PBL from a healthy donor containing initially 2.4% of RO-73+ cells.

From the purified RO-73+ and JU-74+ cells selected in this way, the respective cell lines were established; each line is 100% recognized by the two monoclonal antibodies, which shows that the two monoclonal antibodies recognize the same cells in peripheral blood.

Analysis of TCR transcripts expressed in the PBLs recognized by RO-73 and JU-74 by PCR techniques a) Method of analysing the β transcripts The range of specific oligonucleotides of Vβ segments of type Vβ1 to Vβ24 described above (SEQ ID No. 25 to No. 48) were used as specific primers for analysing the TCR β transcripts expressed in the RO-73+ and JU-74+ cells. The procedure used is identical to that described in the example above for the peripheral lymphocytes of a healthy individual. In brief, after preparation of the RNA according to the Chomczynski method (13), the complementary DNA was synthesized using reverse transcriptase and the CβB primer (SEQ ID No. 50). The material obtained was subjected to 30 amplification cycles according to the PCR technique using in parallel each of the specific Vβ primers corresponding to the sequences SEQ ID No. 25 to 48 and the specific CβB primer of the Cβ region (SEQ ID No. 50) as described previously.

The amplified products obtained were separated by electrophoresis on 2% agarose gel, transferred onto nylon membranes and hybridized with the CβC oligonucleotide probe (SEQ ID No. 51) labelled with $^{32}p$ The membranes were then washed as described above then autoradiographed.

The sequencing of the transcripts of the TCR β chain was carried out following the cloning and sequencing method described previously for the cDNA. For example, the material amplified by the specific oligonucleotide of the Vβ13 sub-family (SEQ ID No. 37) was digested by the enzyme SacII and purified by electrophoresis on agarose gel. The material obtained was introduced into the pBS SK⁺ vector (as described above for the A-PCR technique) and used to transfect the E. Coli XL-1 blue bacteria. The transformed colonies obtained were tested by dot-blot hybridization using the CβC oligonucleotide probe (SEQ ID NO. 51) labelled with $^{32}p$ The plasmid DNA was sequenced as described previously.

b) Method of analysing the transcripts

A methodology resembling that described for the β transcripts was applied to the analysis of the transcripts of the TCR α chain using as specific primers a range of specific oligonucleotides of Vα segments of the Vα1 to Vα29 type and specific oligonucleotides of the constant Cα region (CαB oligonucleotide for the synthesis of the complementary DNA and the amplification by PCR and CαC oligonucleotide for the detection probe). The sequences of these oligonucleotides are indicated in Table 2.

TABLE 2

| Sequence | Type |
| --- | --- |
| 5'-GGCATTAACGGTTTTGAGGCTGGA-3' | Vα1 SEQ ID NO:58 |
| 5'-CAGTGTTCCAGAGGGAGCCATTGC-3' | Vα2 SEQ ID NO:59 |
| 5'-CCGGGCAGCAGAGACACTGCTTCTTA-3' | Vα3 SEQ ID NO:60 |
| 5'-TTGGTATCGACAGCTTCCCTCCCA-3' | Vα4 SEQ ID NO:61 |
| 5'-CGGCCACCCTGACCTGCAACTATA-3' | Vα5 SEQ ID NO:62 |
| 5'-TCCGCCAACCTTGTCATCTCCGCT-3' | Vα6 SEQ ID NO:63 |
| 5'-GCAACATGCTGGCGGAGCACCCAC-3' | Vα7 SEQ ID NO:64 |
| 5'-CATTCGTTCAAATGTGGGCAAAAG-3' | Vα8 SEQ ID NO:65 |
| 5'-CCAGTACTCCAGACAACGCCTGCA-3' | Vα9 SEQ ID NO:66 |
| 5'-CACTGCGGCCCAGCCTGGTGATAC-3' | Vα10 SEQ ID NO:67 |
| 5'-CGCTGCTCATCCTCCAGGTGCGGG-3' | Vα11 SEQ ID NO:68 |
| 5'-TCGTCGGAACTCTTTTGATGAGCA-3' | Vα12 SEQ ID NO:69 |
| 5'-TTCATCAAAACCCTTGGGGACAGC-3' | Vα13 SEQ ID NO:70 |
| 5'-CCCAGCAGGCAGATGATTCTCGTT-3' | Vα14 SEQ ID NO:71 |
| 5'-TTGCAGACACCGAGACTGGGGACT-3' | Vα15 SEQ ID NO:72 |
| 5'-TCAACGTTGCTGAAGGGAATCCTC-3' | Vα16 SEQ ID NO:73 |
| 5'-TGGGAAAGGCCGTGCATTATTGAT-3' | Vα17 SEQ ID NO:74 |
| 5'-CAGCACCAATTTCACCTGCAGCTT-3' | Vα18 SEQ ID NO:75 |
| 5'-ACACTGGCTGCAACAGCATCCAGG-3' | Vα19 SEQ ID NO:76 |
| 5'-TCCCTGTTTATCCCTGCCGACAGA-3' | Vα20 SEQ ID NO:77 |
| 5'-AGCAAAATTCACCATCCCTGAGCG-3' | Vα21 SEQ ID NO:78 |
| 5'-CCTGAAAGCCACGAAGGCTGATGA-3' | Vα22 SEQ ID NO:79 |
| 5'-TGCCTCGCTGGATAAATCATCAGG-3' | Vαw23 SEQ ID NO:80 |
| 5'-CTGGATGCAGACACAAAGCAGAGC-3' | Vαw24 SEQ ID NO:81 |
| 5'-TGGCTACGGTACAAGCCGGACCCT-3' | Vαw25 SEQ ID NO:82 |
| 5'-AGCGCAGCCATGCAGGCATGTACC-3' | Vαw26 SEQ ID NO:83 |
| 5'-AAGCCCGTCTCAGCACCCTCCACA-3' | Vαw27 SEQ ID NO:84 |
| 5'-TGGTTGTGCACGAGCGAGACACTG-3' | Vαw28 SEQ ID NO:85 |
| 5'-GAAGGGTGGAGAACAGATGCGTCG-3' | Vαw29 SEQ ID NO:86 |

TABLE 2-continued

| Sequence | Type |
| --- | --- |
| 5'-ATACACATCAGAATTCTTACTTTG-3' | CαA SEQ ID NO:87 |
| 5'-GTTGCTCCAGGCCGCGGCACTGTT-3' | CαB SEQ ID NO:88 |
| 5'-GTCACTGGATTTAGAGTCT-3' | CαC SEQ ID NO:57 | c) Results

FIG. 13 shows the results obtained for the analysis of transcripts of TCRα chains (FIG. 13A) and β chains (FIG. 13B) expressed by the RO-73+ cells recognized by the monoclonal antibody RO-73. It should be noted that numerous different Vα segments are expressed in these cells (FIG. 13A). On the other hand, only the specific oligonucleotide of the sequences of the Vβ13 sub-family allows an amplification of the cDNA (FIG. 13B).

Identical results were obtained for the TCR β transcripts expressed in the JU-74+ cells recognized by the monoclonal antibody JU-74 (results not shown).

In addition, the β transcripts which correspond to the Vβ13 sub-family expressed by the JU-74+ cells were sequenced from cells previously isolated in order to determine, among. the 5 known or new members of the Vβ13 sub-family (FIG. 4), those whose products are recognized by the monoclonal antibody JU-74. Table 3 shows the results obtained after analysis of these sequences. The eight different sequences of Vβ13 obtained all correspond to a rearrangement of the new Vβ13 genetic segment IGRb16 (SEQ ID No. 15) with different J segments and N regions.

TABLE 3

| | Expression of the transcripts of the β chain in JU-74+ cells | | | |
| --- | --- | --- | --- | --- |
| cDNA clones | Vβ | member | Jβ | Region N |
| B001 | 13 | IGRb16I | J2.1 | ≠ |
| B002 | 13 | IGRb16I | J1.6 | ≠ |
| B006 | 13 | IGRb16I | J1.1 | ≠ |
| B007 | 13 | IGRb16I | J2.1 | ≠ |
| B009 | 13 | IGRb16I | J1.6 | ≠ |
| B010 | 13 | IGRb16I | J2.6 | ≠ |
| B011 | 13 | IGRb16I | J1.3 | ≠ |
| B012 | 13 | IGRb16I | J1.2 | ≠ |

All these results show that the monoclonal antibodies and JU-74 are specific to products of genetic segments nging to the Vβ13 sub-family. More precisely, the monoclonal antibodies JU-74 and RO-73 have the same specificity and recognize exclusively the product of the new Vβ13 genetic segment IGRb16 of the invention. (SEQ ID No. 15 indicated above).

The following hybridoma cell lines were deposited with the Collection Nationale de Culture de Microorganismes (CNCM -Pasteur Institute): JU-74 and RO-73 on the 12th February under the numbers I-1173 and I-1172.

REFERENCES

1. Meuer, S. C., et al., J. Exp. Med. 1983. 157:705.
2. Moingeon, P., et al., Nature 1986a. 323:638.
3. Brenner, M. B., et al., Nature 1986. 322:145.
4. Bank, I., et al., Nature 1986. 322:179.
5. Davis, M. M., et al., Nature 1988. 334:395.
6. Crews, S., et al., Cell 1981. 25:59.
7. Wilson, R.K., et al., Immunological Reviews 1988c. 101:149.

8. Robinson, M. A., Proc. Natl. Acad. Sci. USA 1989. 86:9422.
9. Leiden, J. M., et al., Proc. Natl. Acad. Sci. USA 1986.83:4456.
10. Reynolds 1986.
11. Li, Y., et al., J. Exp. Med. 1990. 171:221.
12. Chirgwin, J. M., et al. Biochemistry 1979. 18:5294.
13. Chomczynski, P., et al., Anal. Biochem. *1987. 162:156.*
14. Saiki, R. K., et al., Science 1988. 239:487.
15. Loh, E. Y., et al., Science 1989. 243:217.
16. Sanger, F., et al., Proc. Natl. Acad. Sci. USA 1977. 20 74:5463.
17. Lipman, D. J., et al., Science 1985. 227:1435.
18. Kozak, M., Nucl. Acids Res. 1984. 12:857.
19. Kyte, J., et al., R. F., J. Mol. Biol. 1982. 157:105.
20. Triebel, F., et al., J. Immun. 1988. 140:300.
21. Feinberg, A. P., et al., Anal. Bichem. 1983. 132:6.
22. Tillinghast, J. P., et al., Science 1986. 248:879.
23. Kimura, N., et al., J. Exp. Med. 1986. 164:739.
24. Concannon, P., et al., Proc.
25. Kimura, N., et al.,Eur. J. Immunol. 1987. 17:375.
26. Duby, A. D., et al., Proc. Natl. Acad. Sc. USA 1986. 83:4890.
27. Naudenbark, A., et al., Nature, 341, 541.
28. Janeway, C., Nature, 341, 482.
29. Lin, Y., J. Exp. Med., 171, 221.
30. Acha-Orbea, H., EMBO Journal, 1990, 9,12, 3815.
31. Kappler, J., Science 244, 811.
32. Choi, Y., PNAS, 86, 8941.
33. Sottini A. et al., Eur. J. Immunol., 1991, 21, 461.
34. Sinha N. et al., Nucleic Acids Res. 1984, 12, 4539.
35. Moebius, U. et al., Eur. J. Immunol. 1990, 20, 889.
36. Hercend, T. et al., Cellular Immunol., 1984, 86, 381.
37. Yoshikai, Y. et al. J. Exp. Med., 1986, 164, 90.
38. Kohler, G. and Milstein, C., Nature, 1975, 256, 495.
39. Kohler, G. Eur. J. Immunol., 1976, 6, 511.
40. Hercend, T. et al., J. Exp. Med., 158, 1983, 1547.
41. Wilson, R.K. et al., Immunogenetics, 1990, 32, 406.

We claim:

1. A hybridoma selected from the group consisting of RO-73 and JU-74, wherein the RO-73 and JU-74 hybridomas produce anti-Vβ13 monoclonal antibodies RO-73 and JU-74 respectively, wherein each of said antibodies recognize exclusively the peptide coded by the nucleotide sequence SEQ ID NO:15, and wherein the RO-73 and JU-74 hybridomas are deposited at Collection Nationale de Culture de Microorganismes (CNCM) on Feb. 12, 1992 under accession numbers I-1172 and I-1173, respectively.

2. An anti-$V_\beta$13 monoclonal antibody selected from the group consisting of RO-73 and JU-74 produced by a hybridoma of claim 1.

* * * * *

SEQUENCE LISTING ( 1 ) GENERAL INFORMATION:

( i i i ) NUMBER OF SEQUENCES: 87

( 2 ) INFORMATION FOR SEQ ID NO:2:

( i ) SEQUENCE CHARACTERISTICS:
        ( A ) LENGTH: 387
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 02
        ( D ) OTHER INFORMATION: V BETA w21

( x i ) SEQUENCE DESCRIPTION: SEQ ID NO:2:

```
AGTGACCCTG ATCTGGCAAA GCTTCCATCC TGCCCTGACC CTGCC ATG                         48
                                                    MET
                                                     1

GGT  ACC  AGG  CTC  CTC  TGC  CGG  GTG  GCC  TTC  TGT  CTC  CTG  GTG  GAA  GAA
Gly  Thr  Arg  Leu  Leu  Cys  Arg  Val  Ala  Phe  Cys  Leu  Leu  Val  Glu  Glu
               5                        10                      15

CTC  ATA  GAA  GCT  GGA  GTG  GTT  CAG  TCT  CCC  AGA  TAT  AAG  ATT  ATA  GAG
Leu  Ile  Glu  Ala  Gly  Val  Val  Gln  Ser  Pro  Arg  Tyr  Lys  Ile  Ile  Glu
               20                       25                      30

AAA  AAG  CAG  CCT  GTG  GCT  TTT  TGG  TGC  AAT  CCT  ATT  TCT  GGC  CAC  AAT
Lys  Lys  Gln  Pro  Val  Ala  Phe  Trp  Cys  Asn  Pro  Ile  Ser  Gly  His  Asn
          35                        40                      45

ACC  CTT  TAC  TGG  TAC  CGG  CAG  AAC  TTG  GGA  CAG  GGC  CCG  GAG  CTT  CTG
Thr  Leu  Tyr  Trp  Tyr  Arg  Gln  Asn  Leu  Gly  Gln  Gly  Pro  Glu  Leu  Leu
 50                       55                        60                      65

ATT  CGA  TAT  GAG  AAT  GAG  GAA  GCA  GTA  GAC  GAT  TCA  CAG  TTG  CCT  AAG
Ile  Arg  Tyr  Glu  Asn  Glu  Glu  Ala  Val  Asp  Asp  Ser  Gln  Leu  Pro  Lys
                         70                       75                      80

GAT  CGA  TTT  TCT  GCA  GAG  AGG  CTC  AAA  GGA  GTA  GAC  TCC  ACT  CTC  AAG
Asp  Arg  Phe  Ser  Ala  Glu  Arg  Leu  Lys  Gly  Val  Asp  Ser  Thr  Leu  Lys
               85                       90                          95
```

```
ATC  CAG  CCT  GCA  GAG  CTT  GGG  GAC  TCG  GCC  GTG  TAT  CTC  TGT  GCC  AGC
Ile  Gln  Pro  Ala  Glu  Leu  Gly  Asp  Ser  Ala  Val  Tyr  Leu  Cys  Ala  Ser
          100                      105                      110

AGC
Ser
```

( 2 ) INFORMATION FOR SEQ ID NO:3:

( i ) SEQUENCE CHARACTERISTICS:
        ( A ) LENGTH: 395
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 03
        ( D ) OTHER INFORMATION: V BETA w22

( x i ) SEQUENCE DESCRIPTION: SEQ ID NO:3:

```
ACAGGACCAG  ATGCCTGAGC  TAGGAAAGGC  CTCATTCCTG  CTGTGATC                              48

CTGCC  ATG  GAT  ACC  TGG  CTC  GTA  TGC  TGG  GCA  ATT  TTT  AGT  CTC  TTG           95
       Met  Asp  Thr  Trp  Leu  Val  Cys  Trp  Ala  Ile  Phe  Ser  Leu  Leu
       1                   5                        10

AAA  GCA  GGA  CTC  ACA  GAA  CCT  GAA  GTC  ACC  CAG  ACT  CCC  AGC  CAT  CAG       143
Lys  Ala  Gly  Leu  Thr  Glu  Pro  Glu  Val  Thr  Gln  Thr  Pro  Ser  His  Gln
15                       20                      25                       30

GTC  ACA  CAG  ATG  GGA  CAG  GAA  GTG  ATC  TTG  CGC  TGT  GTC  CCC  ATC  TCT       191
Val  Thr  Gln  Met  Gly  Gln  Glu  Val  Ile  Leu  Arg  Cys  Val  Pro  Ile  Ser
               35                       40                       45

AAT  CAC  TTA  TAC  TTC  TAT  TGG  TAC  AGA  CAA  ATC  TTG  GGG  CAG  AAA  GTC       239
Asn  His  Leu  Tyr  Phe  Tyr  Trp  Tyr  Arg  Gln  Ile  Leu  Gly  Gln  Lys  Val
               50                       55                       60

GAG  TTT  CTG  GTT  TCC  TTT  TAT  AAT  AAT  GAA  ATC  TCA  GAG  AAG  TGT  GAA       287
Glu  Phe  Leu  Val  Ser  Phe  Tyr  Asn  Asn  Glu  Ile  Ser  Glu  Lys  Ser  Glu
          65                       70                       75

ATA  TTC  GAT  GAT  CAA  TTC  TCA  GTT  GAA  AGG  CCT  GAT  GGA  TCA  AAT  TTC       335
Ile  Phe  Asp  Asp  Gln  Phe  Ser  Val  Glu  Arg  Pro  Asp  Gly  Ser  Asn  Phe
     80                       85                       90

ACT  CTG  AAG  ATC  CGG  TCC  ACA  AAG  CTG  GAG  GAC  TCA  GCC  ATG  TAC  TTC       383
Thr  Leu  Lys  Ile  Arg  Ser  Thr  Lys  Leu  Glu  Asp  Ser  Ala  Met  Tyr  Phe
95                       100                      105                      110

TGT  GCC  AGC  AGT                                                                    395
Cys  Ala  Ser  Ser
```

( 2 ) INFORMATION FOR SEQ ID NO:4:

( i ) SEQUENCE CHARACTERISTICS:
        ( A ) LENGTH: 329
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 04
        ( D ) OTHER INFORMATION: V BETA w23

( x i ) SEQUENCE DESCRIPTION: SEQ ID NO:4:

```
AGCTCCTCTG CCATGTC ATG CTT TGT CTC CTG GGA GCA GGT TCA GTG              47
                    Met Leu Cys Leu Leu Gly Ala Gly Ser Val
                     1           5                      10

GCT GCT GGA GTC ATC CAG TCC CCA AGA CAT CTG ATC AAA GAA AAG AGG         95
Ala Ala Gly Val Ile Gln Ser Pro Arg His Leu Ile Lys Glu Lys Arg
                 15              20                  25

GAA ACA GCC ACT CTG AAA TGC TAT CCT ATC CCT AGA CAC GAC ACT GTC        143
Glu Thr Ala Thr Leu Lys Cys Tyr Pro Ile Pro Arg His Asp Thr Val
             30              35                  40

TAC TGG TAC CAG CAG GGT CCA GGT CAG GAC CCC CAG TTC CTC ATT TCG        191
Tyr Trp Tyr Gln Gln Gly Pro Gly Gln Asp Pro Gln Phe Leu Ile Ser
         45              50                  55

TTT TAT GAA AAG ATG CAG AGC GAT AAA GGA AGC ATC CCT GAT CGA TTC        239
Phe Tyr Glu Lys Met Gln Ser Asp Lys Gly Ser Ile Pro Asp Arg Phe
     60              65                  70

TCA GCT CAA CAG TTC AGT GAC TAT CAT TCT GAA CTG AAC ATG AGC TCC        287
Ser Ala Gln Gln Phe Ser Asp Tyr His Ser Glu Leu Asn Met Ser Ser
 75              80                  85                      90

TTG GAG CTG GGG GAC TCA GCC CTG TAC TTC TGT GCC AGC AGC                329
Leu Gln Leu Gly Asp Ser Ala Leu Tyr Phe Cys Ala Ser Ser
             95                  100
```

( 2 ) INFORMATION FOR SEQ ID NO:5:

( i ) SEQUENCE CHARACTERISTICS:
        ( A ) LENGTH: 366
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 05
        ( D ) OTHER INFORMATION: V BETA w24

( x i ) SEQUENCE DESCRIPTION: SEQ ID NO:5:

```
ATTCCTGTAT GGGGTGGTAT TCCTGCC ATG GGT CCT GGG CTT CTC CAC               48
                             Met Gly Pro Gly Leu Leu His
                              1           5

TGG ATG GCC CTT TGT CTC CTT GGA ACA GGT CAT GGG GAT GCC ATG GTC         96
Trp Met Ala Leu Cys Leu Leu Gly Thr Gly His Gly Asp Ala Met Val
         10              15                  20

ATC CAG AAC CCA AGA TAC CAG GTT ACC CAG TTT GGA AAG CCA GTG ACC        144
Ile Gln Asn Pro Arg Tyr Gln Val Thr Gln Phe Gly Lys Pro Val Thr
     25              30                  35

CTG AGT TGT TCT CAG ACT TTG AAC CAT AAC GTC ATG TAC TGG TAC CAG        192
Leu Ser Cys Ser Gln Thr Leu Asn His Asn Val Met Tyr Trp Tyr Gln
 40              45                  50                      55

CAG AAG TCA AGT CAG GCC CCA AAG CTG CTG TTC CAC TAC TAT GAC AAA        240
Gln Lys Ser Ser Gln Ala Pro Lys Leu Leu Phe His Tyr Tyr Asp Lys
             60                  65                      70

GAT TTT AAC AAT GAA GCA GAC ACC CCT GAT AAC TTC CAA TCC AGG AGG        288
Asp Phe Asn Asn Glu Ala Asp Thr Pro Asp Asn Phe Gln Ser Arg Arg
             75                  80                      85

CCG AAC ACT TCT TTC TGC TTT CTT GAC ATC CGC TCA CCA GGC CTG GGG        336
Pro Asn Thr Ser Phe Cys Phe Leu Asp Ile Arg Ser Pro Gly Leu Gly
             90                  95                      100
```

```
GAC  GCA  GCC  ATG  TAC  CTG  TGT  GCC  ACC  AGC                                              366
Asp  Ala  Ala  Met  Tyr  Leu  Cys  Ala  Thr  Ser
     105            110
```

( 2 ) INFORMATION FOR SEQ ID NO:6:

( i ) SEQUENCE CHARACTERISTICS:
        ( A ) LENGTH: 238
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 06
        ( D ) OTHER INFORMATION: V BETA 5

( x i ) SEQUENCE DESCRIPTION: SEQ ID NO:6:

```
A   GGA  CAG  CAA  GCG  ACT  CTG  AGA  TGC  TCT  CCT  ATC  TCT  GGG  CAC  ACC         4 6
    Gly  Gln  Gln  Ala  Thr  Leu  Arg  Cys  Ser  Pro  Ile  Ser  Gly  His  Thr
    1              5                        10                       15

AGT  GTG  TAC  TGG  TAC  CAA  CAG  GCC  CTG  GGT  CTG  GGC  CTC  CAG  CTC  CTC        94
Ser  Val  Try  Trp  Tyr  Gln  Gln  Ala  Leu  Gly  Leu  Gly  Leu  Gln  Leu  Leu
               20                      25                       30

CTT  TGG  TAT  GAC  GAG  GGT  GAA  GAG  AGA  AAC  AGA  GGA  AAC  TTC  CCT  CCT       142
Leu  Trp  Tyr  Asp  Glu  Gly  Glu  Glu  Arg  Asn  Arg  Gly  Asn  Phe  Pro  Pro
               35                      40                       45

AGA  TTT  TCA  GGT  CGC  CAG  TTC  CCT  AAT  TAT  AGC  TCT  GAG  CTG  AAT  GTG       190
Arg  Phe  Ser  Gly  Arg  Gln  Phe  Pro  Asn  Tyr  Ser  Ser  Glu  Leu  Asn  Val
               50                      55                       60

AAC  GCC  TTG  GAG  CTG  GAG  GAC  TCG  GCC  CTG  TAT  CTC  TGT  GCC  AGC  AGC       238
Asn  Ala  Leu  Glu  Leu  Glu  Asp  Ser  Ala  Leu  Tyr  Leu  Cys  Ala  Ser  Ser
     65                      70                       75
```

( 2 ) INFORMATION FOR SEQ ID NO:7:

( i ) SEQUENCE CHARACTERISTICS:
        ( A ) LENGTH: 192
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 07
        ( D ) OTHER INFORMATION: V BETA 5

( x i ) SEQUENCE DESCRIPTION: SEQ ID NO:7:

```
ACT  GTG  TCC  TGG  TAC  CAA  CAG  GCC  CTG  GGT  CAG  GGG  CCC  CAG  TTT  ATC        48
Thr  Val  Ser  Trp  Tyr  Gln  Gln  Ala  Leu  Gly  Gln  Gly  Pro  Gln  Phe  Ile
1              5                       10                       15

TTT  CAG  TAT  TAT  AGG  GAG  GAA  GAG  AAT  GGC  AGA  GGA  AAC  TCC  CCT  CCT        96
Phe  Gln  Tyr  Tyr  Arg  Glu  Glu  Glu  Asn  Gly  Arg  Gly  Asn  Ser  Pro  Pro
               20                      25                       30

AGA  TTC  TCA  GGT  CTC  CAG  TTC  CCT  AAT  TAT  AGC  TCT  GAG  CTG  AAT  GTG       144
Arg  Phe  Ser  Gly  Leu  Gln  Phe  Pro  Asn  Tyr  Ser  Ser  Glu  Leu  Asn  Val
               35                      40                       45

AAC  GCC  TTG  GAG  CTG  GAC  GAC  TCG  GCC  CTG  TAT  CTC  TGT  GCC  AGC  AGC       192
Asn  Ala  Leu  Glu  Leu  Asp  Asp  Ser  Ala  Leu  Tyr  Leu  Cys  Ala  Ser  Ser
```

(2) INFORMATION FOR SEQ ID NO:8:

(i) SEQUENCE CHARACTERISTICS:
        (A) LENGTH: 410
        (B) TYPE: NUCLEOTIDE
        (C) STRANDEDNESS: DOUBLE
        (D) TOPOLOGY: LINEAR (ii) MOLECULE TYPE: cDNA TO mRNA (vi) ORIGINAL SOURCE:
        (A) ORGANISM: HUMAN
        (H) CELL LINE: HUMAN T LYMPHOCYTE (ix) FEATURE:
        (A) NAME/KEY: IGR b 08
        (D) OTHER INFORMATION: V BETA 5

(xi) SEQUENCE DESCRIPTION: SEQ ID NO:8:

```
GAACTCACTG GGTTCTTCCC CAGGAGGACC AAGCCCTGAA TCAGGTGCAG                                    50

TGCTGCCTGC CCCACTGTGC C ATG GGC CCT GGG CTC CTC TGC TGG                                    95
                        Met Gly Pro Gly Leu Leu Cys Trp
                         1           5

GTG CTG CTT TGT CTC CTG GGA GCA GGC CCA GTG GAC GCT GGA GTC ACC                           143
Val Leu Leu Cys Leu Leu Gly Ala Gly Pro Val Asp Ala Gly Val Thr
     10              15                  20

CAA AGT CCC ACA CAC CTG ATC AAA ACG AGA GGA CAG CAA GTG ACT CTG                           191
Gln Ser Pro Thr His Leu Ile Lys Thr Arg Gly Gln Gln Val Thr Leu
 25              30                  35                      40

AGA TGC TCT CCT ATC TCT GAG CAC AAG AGT GTG TCC TGG TAC CAA CAG                           239
Arg Cys Ser Pro Ile Ser Glu His Lys Ser Val Ser Trp Tyr Gln Gln
                 45                  50                      55

GTC CTG GGT CAG GGG CCC CAG TTT ATC TTT CAG TAT TAT GAG AAA GAA                           287
Val Leu Gly Gln Gly Pro Gln Phe Ile Phe Gln Tyr Tyr Glu Lys Glu
             60                  65                  70

GAG AGA GGA AGA GGA AAC TTC CCT GAT CGA TTC TCA GCT CGC CAG TTC                           335
Glu Arg Gly Arg Gly Asn Phe Pro Asp Arg Phe Ser Ala Arg Gln Phe
         75                  80                  85

CCT AAC TAT AGC TCT GAG CTG AAT GTG AAC GCC TTG TTG CTG GGG GAC                           383
Pro Asn Tyr Ser Ser Glu Leu Asn Val Asn Ala Leu Leu Leu Gly Asp
     90                  95                 100

TCG GCC CTG TAT CTC TGT GCC AGC AGC                                                       410
Ser Ala Leu Tyr Leu Cys Ala Ser Ser
105                 110
```

(2) INFORMATION FOR SEQ ID NO:9:

(i) SEQUENCE CHARACTERISTICS:
        (A) LENGTH: 380
        (B) TYPE: NUCLEOTIDE
        (C) STRANDEDNESS: DOUBLE
        (D) TOPOLOGY: LINEAR (ii) MOLECULE TYPE: cDNA TO mRNA (vi) ORIGINAL SOURCE:
        (A) ORGANISM: HUMAN
        (H) CELL LINE: HUMAN T LYMPHOCYTE (ix) FEATURE:
        (A) NAME/KEY: IGR b 09
        (D) OTHER INFORMATION: V BETA 5

(xi) SEQUENCE DESCRIPTION: SEQ ID NO:9:

```
AAGCCCTGAA TCAGATGCAG TGCTTCCTGT CCCTCTGTGC C ATG GGC                                      47
                                              Met Gly
```

```
CCC  GGG  CTC  CTC  TGC  TGG  GCA  CTG  CTT  TGT  CTC  CTG  GGA  GCA  GGC  TTA         95
Pro  Gly  Leu  Leu  Cys  Trp  Ala  Leu  Leu  Cys  Leu  Leu  Gly  Ala  Gly  Leu
          5                        10                      15

GTG  GAC  GCT  GGA  GTC  ACC  CAA  AGT  CCC  ACA  CAC  CTG  ATC  AAA  ACG  AGA         143
Val  Asp  Ala  Gly  Val  Thr  Gln  Ser  Pro  Thr  His  Leu  Ile  Lys  Thr  Arg
     20                       25                      30

GGA  CAG  CAA  GTG  ACT  CTG  AGA  TGC  TCT  CCT  AAG  TCT  GGG  CAT  GAC  ACT         191
Gly  Gln  Gln  Val  Thr  Leu  Arg  Cys  Ser  Pro  Lys  Ser  Gly  His  Asp  Thr
35                       40                       45                           50

GTG  TCC  TGG  TAC  CAA  CAG  GCC  CTG  GGT  CAG  GGG  CCC  CAG  TTT  ATC  TTT         239
Val  Ser  Trp  Tyr  Gln  Gln  Ala  Leu  Gly  Gln  Gly  Pro  Gln  Phe  Ile  Phe
                    55                       60                      65

CAG  TAT  TAT  GAG  GAG  GAA  GAG  AGA  CAG  AGA  GGC  AAC  TTC  CCT  GAT  CGA         287
Gln  Tyr  Tyr  Glu  Glu  Glu  Glu  Arg  Gln  Arg  Gly  Asn  Phe  Pro  Asp  Arg
               70                       75                      80

TTC  TCA  GGT  CAC  CAG  TTC  CCT  AAC  TAT  AGC  TCT  GAG  CTG  AAT  GTG  AAC         335
Phe  Ser  Gly  His  Gln  Phe  Pro  Asn  Tyr  Ser  Ser  Glu  Leu  Asn  Val  Asn
          85                       90                      95

GCC  TTG  TTG  CTG  GGG  GAC  TCG  GCC  CTC  TAT  CTC  TGT  GCC  AGC  AGC              380
Ala  Leu  Leu  Leu  Gly  Asp  Ser  Ala  Leu  Tyr  Leu  Cys  Ala  Ser  Ser
100                      105                      110
```

( 2 ) INFORMATION FOR SEQ ID NO:10:

( i ) SEQUENCE CHARACTERISTICS:
        ( A ) LENGTH: 351
        ( B ) TYPE: NUCLEOTIDE
        ( C ) STRANDEDNESS: DOUBLE
        ( D ) TOPOLOGY: LINEAR ( i i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 11
        ( D ) OTHER INFORMATION: V BETA 6

( x i ) SEQUENCE DESCRIPTION: SEQ ID NO:10:

```
GACCCTGCC  ATG  GGC  ACC  AGT  CTC  CTA  TGC  TGG  GTG  GTC  CTG  GGT  TTC            48
           Met  Gly  Thr  Ser  Leu  Leu  Cys  Trp  Val  Val  Leu  Gly  Phe
            1                   5                           10

CTA  GGG  ACA  GAT  CAC  ACA  GGT  GCT  GGA  GTC  TCC  CAG  TCT  CCC  AGG  TAC         96
Leu  Gly  Thr  Asp  His  Thr  Gly  Ala  Gly  Val  Ser  Gln  Ser  Pro  Arg  Tyr
          15                       20                      25

AAA  GTC  ACA  AAG  AGG  GGA  CAG  GAT  GTA  GCT  CTC  AGG  TGT  GAT  CCA  ATC         144
Gln  Val  Thr  Lys  Arg  Gly  Gln  Asp  Val  Ala  Leu  Arg  Cys  Asp  Pro  Ile
30                       35                       40                           45

TCG  GGT  CAT  GTA  TCC  CTT  TAT  TGG  TAC  CGA  CAG  GCC  CTG  GGG  CAG  GGC         192
Ser  Gly  His  Val  Ser  Leu  Tyr  Trp  Tyr  Arg  Gln  Ala  Leu  Gly  Gln  Gly
                    50                       55                      60

CCA  GAG  TTT  CTG  ACT  TAC  TTC  AAT  TAT  GAA  GCC  CAA  CAA  GAC  AAA  TCA         240
Pro  Glu  Phe  Leu  Thr  Tyr  Phe  Asn  Tyr  Glu  Ala  Gln  Gln  Asp  Lys  Ser
               65                       70                      75

GGG  CTG  CCC  AAT  GAT  CGG  TTC  TCT  GCA  GAG  AGG  CCT  GAG  GGA  TCC  ATC         288
Gly  Leu  Pro  Asn  Asp  Arg  Phe  Ser  Ala  Glu  Arg  Pro  Glu  Gly  Ser  Ile
          80                       85                      90

TCC  ACT  CTG  ACG  ATC  CAG  CGC  ACA  GAG  CAG  CGG  GAC  TCG  GCC  ATG  TAT         336
Ser  Thr  Leu  Thr  Ile  Gln  Arg  Thr  Glu  Gln  Arg  Asp  Ser  Ala  Met  Tyr
          95                       100                     105

CGC  TGT  GCC  AGC  AGC                                                                351
```

Arg Cys Ala Ser Ser
110

(2) INFORMATION FOR SEQ ID NO:11:

(i) SEQUENCE CHARACTERISTICS:
        (A) LENGTH: 238
        (B) TYPE: NUCLEOTIDE
        (C) STRANDEDNESS: DOUBLE
        (D) TOPOLOGY: LINEAR (ii) MOLECULE TYPE: cDNA TO mRNA (vi) ORIGINAL SOURCE:
        (A) ORGANISM: HUMAN
        (H) CELL LINE: HUMAN T LYMPHOCYTE (ix) FEATURE:
        (A) NAME/KEY: IGR b 12
        (D) OTHER INFORMATION: V BETA 6

(xi) SEQUENCE DESCRIPTION: SEQ ID NO:11:

```
A  AAG  GAT  GTA  GAG  CTC  AGG  TGT  GAT  CCA  ATT  TCA  GGT  CAT  ACT  GCC        4
   Lys  Asp  Val  Glu  Leu  Arg  Cys  Asp  Pro  Ile  Ser  Gly  His  Thr  Ala
   1                  5                        10                       15

CTT  TAC  TGG  TAC  CGA  CAG  AGC  CTG  GGG  CAG  GGC  CTG  GAG  TTT  TTA  ATT      94
Leu  Tyr  Trp  Tyr  Arg  Gln  Ser  Leu  Gly  Gln  Gly  Leu  Glu  Phe  Leu  Ile
                    20                      25                       30

TAC  TTC  CAA  GGC  AAC  AGT  GCA  CCA  GAC  AAA  TCA  GGG  CTG  CCC  AAC  GAT     142
Tyr  Phe  Gln  Gly  Asn  Ser  Ala  Pro  Asp  Lys  Ser  Gly  Leu  Pro  Asn  Asp
               35                        40                  45

CGG  TTC  TTT  GCA  GTC  AGG  CCT  GAG  GGA  TCC  GTC  TCT  ACT  CTG  AGG  ATC     190
Arg  Phe  Phe  Ala  Val  Arg  Pro  Glu  Gly  Ser  Val  Ser  Thr  Leu  Arg  Ile
          50                        55                       60

CAG  CGC  ACA  GAG  CGG  GGG  GAC  TCA  GCC  GTG  TAT  CTC  TGT  GCC  AGC  AGC     238
Gln  Arg  Thr  Glu  Arg  Gly  Asp  Ser  Ala  Val  Tyr  Leu  Cys  Ala  Ser  Ser
     65                       70                       75
```

(2) INFORMATION FOR SEQ ID NO:12:

(i) SEQUENCE CHARACTERISTICS:
        (A) LENGTH: 294
        (B) TYPE: NUCLEOTIDE
        (C) STRANDEDNESS: DOUBLE
        (D) TOPOLOGY: LINEAR (ii) MOLECULE TYPE: cDNA TO mRNA (vi) ORIGINAL SOURCE:
        (A) ORGANISM: HUMAN
        (H) CELL LINE: HUMAN T LYMPHOCYTE (ix) FEATURE:
        (A) NAME/KEY: IGR b 13
        (D) OTHER INFORMATION: V BETA 12

(xi) SEQUENCE DESCRIPTION: SEQ ID NO:12:

```
TCA  GGA  CAC  AGG  GAT  GCT  GAA  ATC  ACC  CAG  AGC  CCA  AGA  CAC  AAG  ATC      48
Ser  Gly  His  Arg  Asp  Ala  Glu  Ile  Thr  Gln  Ser  Pro  Arg  His  Lys  Ile
1                  5                        10                       15

ACA  GAG  ACA  GGA  AGG  CAG  GTG  ACC  TTG  GCG  TGT  CAC  CAG  ACT  TGG  AAC      96
Thr  Glu  Thr  Gly  Arg  Gln  Val  Thr  Leu  Ala  Cys  His  Gln  Thr  Trp  Asn
               20                       25                       30

CAC  AAC  AAT  ATG  TTC  TGG  TAT  CGA  CAA  GAC  CTG  GGA  CAT  GGG  CTG  AGG     144
His  Asn  Asn  Met  Phe  Trp  Tyr  Arg  Gln  Asp  Leu  Gly  His  Gly  Leu  Arg
               35                        40                  45

CTG  ATC  CAT  TAC  TCA  TAT  GGT  GTT  CAA  GAC  ACT  AAC  AAA  GGA  GAA  GTC     192
Leu  Ile  His  Tyr  Ser  Tyr  Gly  Val  Gln  Asp  Thr  Asn  Lys  Gly  Glu  Val
          50                       55                       60
```

```
TCA GAT GGC TAC AGT GTC TCT AGA TCA AAC ACA GAG GAC CTC CCC CTC         240
Ser Asp Gly Tyr Ser Val Ser Arg Ser Asn Thr Glu Asp Leu Pro Leu
 65              70                  75                      80

ACT CTG GAG TCT GCT GCC TCC TCC CAG ACA TCT GTA TAT TTC TGC GCC         288
Thr Leu Glu Ser Ala Ala Ser Ser Gln Thr Ser Val Tyr Phe Cys Ala
                 85              90              95

AGC AGG                                                                 294
Ser Ser
```

( 2 ) INFORMATION FOR SEQ ID NO:13:

( i ) SEQUENCE CHARACTERISTICS:
        ( A ) LENGTH: 369
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 14
        ( D ) OTHER INFORMATION: V BETA 13

( x i ) SEQUENCE DESCRIPTION: SEQ ID NO:13:

```
AGAAGACCCC TCCATCCTGT AGCACCTGCC ATG AGC ATC GGG CTC CTG                 48
                                 Met Ser Ile Gly Leu Leu
                                  1               5

TGC TGT GTG GCC TTT TCT CTC CTG TGG GCA AGT CCA GTG AAT GCT GGT          96
Cys Cys Val Ala Phe Ser Leu Leu Trp Ala Ser Pro Val Asn Ala Gly
             10              15              20

GTC ACT CAG ACC CCA AAA TTC CAG GTC CTG AAG ACA GGA CAG AGC ATG         144
Val Thr Gln Thr Pro Lys Phe Gln Val Leu Lys Thr Gly Gln Ser Met
         25              30              35

ACA CTG CAG TGT GCC CAG GAT ATG AAC CAT AAC TCC ATG TAC TGG TAT         192
Thr Leu Gln Cys Ala Gln Asp Met Asn His Asn Ser Met Tyr Trp Tyr
     40              45              50

CGA CAA GAC CCA GGC ATG GGA CTG AGG CTG ATT TAT TAC TCA GCT TCT         240
Arg Gln Asp Pro Gly Met Gly Leu Arg Leu Ile Tyr Tyr Ser Ala Ser
 55              60              65              70

GAG GGT ACC ACT GAC AAA GGA GAA GTC CCC AAT GGC TAC AAT GTC TCC         288
Glu Gly Thr Thr Asp Lys Gly Glu Val Pro Asn Gly Tyr Asn Val Ser
             75              80              85

AGA TTA AAC AAA CGG GAG TTC TCG CTC AGG CTG GAG TCG GCT GCT CCC         336
Arg Leu Asn Lys Arg Glu Phe Ser Leu Arg Leu Glu Ser Ala Ala Pro
             90              95              100

TCC CAG ACA TCT GTG TAC TTC TGT GCC AGC ACC                             369
Ser Gln Thr Ser Val Tyr Phe Cys Ala Ser Thr
         105             110
```

( 2 ) INFORMATION FOR SEQ ID NO:14:

( i ) SEQUENCE CHARACTERISTICS:
        ( A ) LENGTH: 356
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE (ix) FEATURE:
  (A) NAME/KEY: IGR b 15
  (D) OTHER INFORMATION: V BETA 13

(xi) SEQUENCE DESCRIPTION: SEQ ID NO:14:

| TGCTTGTAGC | ATCTGCC | ATG | AGA | ATC | AGG | CTC | CTG | TGC | TGT | GTG | GCC | | 47 |
|---|---|---|---|---|---|---|---|---|---|---|---|---|---|
| | | Met | Arg | Ile | Arg | Leu | Leu | Cys | Cys | Val | Ala | | |
| | | 1 | | | 5 | | | | | | 10 | | |

| TTT | TCT | CTC | CTG | TGG | GCA | GGT | CCA | GTG | ATT | GCT | GGG | ATC | ACC | CAG | GCA | 95 |
|---|---|---|---|---|---|---|---|---|---|---|---|---|---|---|---|---|
| Phe | Ser | Leu | Leu | Trp | Ala | Gly | Pro | Val | Ile | Ala | Gly | Ile | Thr | Gln | Ala | |
| | | | | 15 | | | | | 20 | | | | | 25 | | |

| CCA | ACA | TCT | CAG | ATC | CTG | GCA | GCA | GGA | CGG | CGC | ATG | ACA | CTG | AGA | TGT | 143 |
|---|---|---|---|---|---|---|---|---|---|---|---|---|---|---|---|---|
| Pro | Thr | Ser | Gln | Ile | Leu | Ala | Ala | Gly | Arg | Arg | Met | Thr | Leu | Arg | Cys | |
| | | | 30 | | | | | 35 | | | | | 40 | | | |

| ACC | CAG | GAT | ATG | AGA | CAT | AAT | GCC | ATG | TAC | TGG | TAT | AGA | CAA | GAT | CTA | 191 |
|---|---|---|---|---|---|---|---|---|---|---|---|---|---|---|---|---|
| Thr | Gln | Asp | Met | Arg | His | Asn | Ala | Met | Tyr | Trp | Tyr | Arg | Gln | Asp | Leu | |
| | | | 45 | | | | 50 | | | | | 55 | | | | |

| GGA | CTG | GGG | CTA | AGG | CTC | ATC | CAT | TAT | TCA | AAT | ACT | GCA | GGT | ACC | ACT | 239 |
|---|---|---|---|---|---|---|---|---|---|---|---|---|---|---|---|---|
| Gly | Leu | Gly | Leu | Arg | Leu | Ile | His | Tyr | Ser | Asn | Thr | Ala | Gly | Thr | Thr | |
| | 60 | | | | | 65 | | | | | 70 | | | | | |

| GGC | AAA | GGA | GAA | GTC | CCT | GAT | GGT | TAT | AGT | GTC | TCC | AGA | GCA | AAC | ACA | 287 |
|---|---|---|---|---|---|---|---|---|---|---|---|---|---|---|---|---|
| Gly | Lys | Gly | Glu | Val | Pro | Asp | Gly | Tyr | Ser | Val | Ser | Arg | Ala | Asn | Thr | |
| 75 | | | | | 80 | | | | | 85 | | | | | 90 | |

| GAT | GAT | TTC | CCC | CTC | ACG | TTG | GCG | TCT | GCT | GTA | CCC | TCT | CAG | ACA | TCT | 335 |
|---|---|---|---|---|---|---|---|---|---|---|---|---|---|---|---|---|
| Asp | Asp | Phe | Pro | Leu | Thr | Leu | Ala | Ser | Ala | Val | Pro | Ser | Gln | Thr | Ser | |
| | | | | 95 | | | | | 100 | | | | | 105 | | |

| GTG | TAC | TTC | TGT | GCC | AGC | AGT | 356 |
|---|---|---|---|---|---|---|---|
| Val | Tyr | Phe | Cys | Ala | Ser | Ser | |
| | | | 110 | | | | |

(2) INFORMATION FOR SEQ ID NO:15:

(i) SEQUENCE CHARACTERISTICS:
    (A) LENGTH: 345
    (B) TYPE: NUCLEOTIDE
    (C) STRANDEDNESS: DOUBLE
    (D) TOPOLOGY: LINEAR (ii) MOLECULE TYPE: cDNA TO mRNA (vi) ORIGINAL SOURCE:
    (A) ORGANISM: HUMAN
    (H) CELL LINE: HUMAN T LYMPHOCYTE (ix) FEATURE:
    (A) NAME/KEY: IGR b 16
    (D) OTHER INFORMATION: V BETA (xi) SEQUENCE DESCRIPTION: SEQ ID NO:15:

| AAGCCCAGC | CCCTTTCCAT | TGGGGCTGCA | GCATCAGCTG | TTTCCTTCTC | 50 |
|---|---|---|---|---|---|

| TGCAGGT | CCA | GTG | AAT | GCT | GGT | GTC | ACT | CAG | ACC | CCA | AAA | TTC | CGC | 96 |
|---|---|---|---|---|---|---|---|---|---|---|---|---|---|---|
| | Pro | Val | Asn | Ala | Gly | Val | Thr | Gln | Thr | Pro | Lys | Phe | Arg | |
| | 1 | | | | 5 | | | | | 10 | | | | |

| ATC | CTG | AAG | ATA | GGA | CAG | AGC | ATG | ACA | CTG | CAG | TGT | GCC | CAG | GAT | ATG | 144 |
|---|---|---|---|---|---|---|---|---|---|---|---|---|---|---|---|---|
| Ile | Leu | Lys | Ile | Gly | Gln | Ser | Met | Thr | Leu | Gln | Cys | Ala | Gln | Asp | Met | |
| | | 15 | | | | | 20 | | | | | 25 | | | | |

| AAC | CAT | AAC | TAC | ATG | TAC | TGG | TAT | CGA | CAA | GAC | CCA | GGC | ATG | GGG | CTG | 192 |
|---|---|---|---|---|---|---|---|---|---|---|---|---|---|---|---|---|
| Asn | His | Asn | Tyr | Met | Tyr | Trp | Tyr | Arg | Gln | Asp | Pro | Gly | Met | Gly | Leu | |
| 30 | | | | | 35 | | | | | 40 | | | | | 45 | |

| AAG | CTG | ATT | TAT | TAT | TCA | GTT | GGT | GCT | GGT | ATC | ACT | GAT | AAA | GGA | GAA | 240 |
|---|---|---|---|---|---|---|---|---|---|---|---|---|---|---|---|---|
| Lys | Leu | Ile | Tyr | Tyr | Ser | Val | Gly | Ala | Gly | Ile | Thr | Asp | Lys | Gly | Glu | |
| | | | | 50 | | | | | 55 | | | | | 60 | | |

| GTC | CCG | AAT | GGC | TAC | AAC | GTC | TCC | AGA | TCA | ACC | ACA | GAG | GAT | TTC | CCG | 288 |
|---|---|---|---|---|---|---|---|---|---|---|---|---|---|---|---|---|
| Val | Pro | Asn | Gly | Tyr | Asn | Val | Ser | Arg | Ser | Thr | Thr | Glu | Asp | Phe | Pro | |
| | | | 65 | | | | | 70 | | | | | 75 | | | |

```
CTC  AGG  CTG  GAG  TTG  GCT  GCT  CCC  TCC  CAG  ACA  TCT  GTG  TAC  TTC  TGT      336
Leu  Arg  Leu  Glu  Leu  Ala  Ala  Pro  Ser  Gln  Thr  Ser  Val  Tyr  Phe  Cys
          80                      85                     90

GCC  AGC  AGT                                                                       345
Ala  Ser  Ser
          95
```

( 2 ) INFORMATION FOR SEQ ID NO:16:

( i ) SEQUENCE CHARACTERISTICS:
      ( A ) LENGTH: 450
      ( B ) TYPE: NUCLEOTIDE
      ( C ) STRANDEDNESS: DOUBLE
      ( D ) TOPOLOGY: LINEAR ( i i ) MOLECULE TYPE: cDNA TO mRNA ( v i ) ORIGINAL SOURCE:
      ( A ) ORGANISM: HUMAN
      ( H ) CELL LINE: HUMAN T LYMPHOCYTE ( i x ) FEATURE:
      ( A ) NAME/KEY: IGR b 17
      ( D ) OTHER INFORMATION: V BETA 7

( x i ) SEQUENCE DESCRIPTION: SEQ ID NO:16:

```
                              TGGAGCAGTG  ACATCACAGG  AAAAACCACC  AACCAAGGCC    40

AAGGAGACCA  GAGCCCAGCA  CCTCACCCAG  AGGACCCCAG  TCAGAGGCCC  CATCTCAGAC          100

CCGAGGCTAG  C  ATG  GGC  TGC  AGG  CTG  CTC  TGC  TGT  GCG  GTT  CTC           144
               Met  Gly  Cys  Arg  Leu  Leu  Cys  Cys  Ala  Val  Leu
                1              5                              10

TGT  CTC  CTG  GGA  GCG  GTC  CCC  ATG  GAA  ACG  GGA  GTT  ACG  CAG  ACA  CCA  192
Cys  Leu  Leu  Gly  Ala  Val  Pro  Met  Glu  Thr  Gly  Val  Thr  Gln  Thr  Pro
          15                      20                          25

AGA  CAC  CTG  GTC  ATG  GGA  ATG  ACA  AAT  AAG  AAG  TCT  TTG  AAA  TGT  GAA  240
Arg  His  Leu  Val  Met  Gly  Met  Thr  Asn  Lys  Lys  Ser  Leu  Lys  Cys  Glu
          30                      35                          40

CAA  CAT  CTG  GGG  CAT  AAC  GCT  ATG  TAT  TGG  TAC  AAG  CAA  AGT  GCT  AAG  288
Gln  His  Leu  Gly  His  Asn  Ala  Met  Tyr  Trp  Tyr  Lys  Gln  Ser  Ala  Lys
     45                      50                          55

AAG  CCA  CTG  GAG  CTC  ATG  TTT  GTC  TAC  AAC  TTT  AAA  GAA  CAG  ACT  GAA  336
Lys  Pro  Leu  Glu  Leu  Met  Phe  Val  Tyr  Asn  Phe  Lys  Glu  Gln  Thr  Glu
60                      65                          70                      75

AAC  AAC  AGT  GTG  CCA  AGT  CGC  TTC  TCA  CCT  GAA  TGC  CCC  AAC  AGC  TCT  384
Asn  Asn  Ser  Val  Pro  Ser  Arg  Phe  Ser  Pro  Glu  Cys  Pro  Asn  Ser  Ser
               80                      85                          90

CAC  TTA  TGC  CTT  CAC  CTA  CAC  ACC  CTG  CAG  CCA  GAA  GAC  TCG  GCC  CTG  432
His  Leu  Cys  Leu  His  Leu  His  Thr  Leu  Gln  Pro  Glu  Asp  Ser  Ala  Leu
               95                      100                         105

TAT  CTC  TGT  GCC  AGC  ACC                                                    450
Tyr  Leu  Cys  Ala  Ser  Thr
          110
```

( 2 ) INFORMATION FOR SEQ ID NO:17:

( i ) SEQUENCE CHARACTERISTICS:
      ( A ) LENGTH: 354
      ( B ) TYPE: NUCLEOTIDE
      ( C ) STRANDEDNESS: DOUBLE
      ( D ) TOPOLOGY: LINEAR ( i i ) MOLECULE TYPE: cDNA TO mRNA ( v i ) ORIGINAL SOURCE:
      ( A ) ORGANISM: HUMAN
      ( H ) CELL LINE: HUMAN T LYMPHOCYTE ( i x ) FEATURE:
  ( A ) NAME/KEY: IGR b 18
  ( D ) OTHER INFORMATION: V BETA 7

( x i ) SEQUENCE DESCRIPTION: SEQ ID NO:17:

```
AGACCCGAGG CTAGC ATG GGC TGC AGG CTG CTC TGC TCT GCG GTT CTC            48
                Met Gly Cys Arg Leu Leu Cys Ser Ala Val Leu
                1               5                       10

TGT CTC CTG GGA GCG GTC CCC ATG GAA ACG GGA GTT ACG CAG ACA CCA          96
Cys Leu Leu Gly Ala Val Pro Met Glu Thr Gly Val Thr Gln Thr Pro
            15              20                  25

AGA CAC CTG GTC ATG GGA ATG ACA AAT AAG AAG TCT TTG AAA TGT GAA         144
Arg His Leu Val Met Gly Met Thr Asn Lys Lys Ser Leu Lys Cys Glu
        30              35                  40

CAA CAT CTG GGT CAT AAC GCT ATG TAT TGG TAC AAG CAA AGT GCT AAG         192
Gln His Leu Gly His Asn Ala Met Tyr Trp Tyr Lys Gln Ser Ala Lys
    45              50                  55

AAG CCA CTG GAG CTC ATG TTT GTC TAC AGT CTT GAA GAA CGG GTT GAA         240
Lys Pro Leu Glu Leu Met Phe Val Tyr Ser Leu Glu Glu Arg Val Glu
60              65                  70                      75

AAC AAC AGT GTG CCA AGT CGC TTC TCA CCT GAA TGC CCC AAC AGC TCT         288
Asn Asn Ser Val Pro Ser Arg Phe Ser Pro Glu Cys Pro Asn Ser Ser
                80                  85              90

CAC TTA TCC CTT CAC CTA CAC ACC CTG CAG CCA GAA GAC TCG GCC CTG         336
His Leu Ser Leu His Leu His Thr Leu Gln Pro Glu Asp Ser Ala Leu
            95              100                 105

TAT CTC TGC GCC AGC AGC                                                 354
Tyr Leu Cys Ala Ser Ser
            110
```

( 2 ) INFORMATION FOR SEQ ID NO:18:

( i ) SEQUENCE CHARACTERISTICS:
    ( A ) LENGTH: 368
    ( B ) TYPE: NUCLEOTIDE
    ( C ) STRANDEDNESS: DOUBLE
    ( D ) TOPOLOGY: LINEAR ( i i ) MOLECULE TYPE: cDNA TO mRNA ( v i ) ORIGINAL SOURCE:
    ( A ) ORGANISM: HUMAN
    ( H ) CELL LINE: HUMAN T LYMPHOCYTE ( i x ) FEATURE:
    ( A ) NAME/KEY: IGR b 19
    ( D ) OTHER INFORMATION: V BETA 7

( x i ) SEQUENCE DESCRIPTION: SEQ ID NO:18:

```
AGAGGCCCCA TCTCAGACCC GAGGCTAGC ATG GGC TGC AGG CTG CTC                  47
                                Met Gly Cys Arg Leu Leu
                                1               5

TGC TGT GCG GTT CTC TGT CTC CTG GGA GCA GTT CCC ATA GAC ACT GAA          95
Cys Cys Ala Val Leu Cys Leu Leu Gly Ala Val Pro Ile Asp Thr Glu
            10              15                  20

GTT ACC CAG ACA CCA AAA CAC CTG GTC ATG GGA ATG ACA AAT AAG AAG         143
Val Thr Gln Thr Pro Lys His Leu Val Met Gly Met Thr Asn Lys Lys
        25              30                  35

TCT TTG AAA TGT GAA CAA CAT ATG GGG CAC AGG GCT ATG TAT TGG TAC         191
Ser Leu Lys Cys Glu Gln His Met Gly His Arg Ala Met Tyr Trp Tyr
    40              45                  50

AAG CAG AAA GCT AAG AAG CCA CCG GAG CTC ATG TTT GTC TAC AGC TAT         239
Lys Gln Lys Ala Lys Lys Pro Pro Glu Leu Met Phe Val Tyr Ser Tyr
55              60                  65                      70
```

```
GAG  AAA  CTC  TCT  ATA  AAT  GAA  AGT  GTG  CCA  AGT  CGC  TTC  TCA  CCT  GAA        287
Glu  Lys  Leu  Ser  Ile  Asn  Glu  Ser  Val  Pro  Ser  Arg  Phe  Ser  Pro  Glu
                    75                   80                         85

TGC  CCC  AAC  AGC  TCT  CTC  TTA  AAC  CTT  CAC  CTA  CAC  GCC  CTG  CAG  CCA        335
Cys  Pro  Asn  Ser  Ser  Leu  Leu  Asn  Leu  His  Leu  His  Ala  Leu  Gln  Pro
               90                        95                        100

GAA  GAC  TCA  GCC  CTG  TAT  CTC  TGC  GCC  AGC  AGC                                  368
Glu  Asp  Ser  Ala  Leu  Tyr  Leu  Cys  Ala  Ser  Ser
          105                      110
```

( 2 ) INFORMATION FOR SEQ ID NO:19:

( i ) SEQUENCE CHARACTERISTICS:
        ( A ) LENGTH: 432
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( H ) CELL LINE: HUMAN T LYMPHOCYTE ( i x ) FEATURE:
        ( A ) NAME/KEY: IGR b 20
        ( D ) OTHER INFORMATION: V BETA 9

( x i ) SEQUENCE DESCRIPTION: SEQ ID NO:19:

```
ACCTCTCAAC  GGCAGTGAAA  CCACAGCCTA  GTCCTCTCAC                                           40

CACTGCAGAC  CAGAATCCTG  CCCTGGGCCT  TGCCTGGTCT  GCCTCACTCT  GCC  ATG                     96
                                                                MET
                                                                1

GGC  TGC  AGG  CTC  CTC  TGC  TGT  GTG  GTC  TTC  TGC  CTC  CTC  CAA  GCA  GGT         144
Gly  Cys  Arg  Leu  Leu  Cys  Cys  Val  Val  Phe  Cys  Leu  Leu  Gln  Ala  Gly
               5                        10                        15

CCC  TTG  GAC  ACA  GCT  GTT  TCC  CAG  ACT  CCA  AAA  TAC  CTG  GTC  ACA  CAG         192
Pro  Leu  Asp  Thr  Ala  Val  Ser  Gln  Thr  Pro  Lys  Tyr  Leu  Val  Thr  Gln
          20                        25                        30

ATG  GGA  AAC  GAC  AAG  TCC  ATT  AAA  TGT  GAA  CAA  AAT  CTG  GGC  CAT  GAT         240
Met  Gly  Asn  Asp  Lys  Ser  Ile  Lys  Cys  Glu  Gln  Asn  Leu  Gly  His  Asp
     35                        40                        45

ACT  ATG  TAT  TGG  TAT  AAA  CAG  GAC  TCT  AAG  AAA  TTT  CTG  AAG  ATA  ATG         288
Thr  Met  Tyr  Trp  Tyr  Lys  Gln  Asp  Ser  Lys  Lys  Phe  Leu  Lys  Ile  Met
50                        55                        60                        65

TTT  AGC  TAC  AAT  AAT  AAG  GAG  CTC  ATT  ATA  AAT  GAA  ACA  GTT  CCA  AAT         336
Phe  Ser  Tyr  Asn  Asn  Lys  Glu  Leu  Ile  Ile  Asn  Glu  Thr  Val  Pro  Asn
                    70                        75                        80

CGC  TTC  TCA  CCT  AAA  TCT  CCA  GAC  AAA  GCT  CAC  TTA  AAT  CTT  CAC  ATC         384
Arg  Phe  Ser  Pro  Lys  Ser  Pro  Asp  Lys  Ala  His  Leu  Asn  Leu  His  Ile
               85                        90                        95

AAT  TCC  CTG  GAG  CTT  GGT  GAC  TCT  GCT  GTG  TAT  TTC  TGT  GCC  AGC  AGC         432
Asn  Ser  Leu  Glu  Leu  Gly  Asp  Ser  Ala  Val  Tyr  Phe  Cys  Ala  Ser  Ser
          100                       105                       110
```

( 2 ) INFORMATION FOR SEQ ID NO:20:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:

( D ) OTHER INFORMATION: PRIMER A ( x i ) SEQUENCE DESCRIPTION: SEQ ID NO:20:

TATCTGGAGT CATTGAGGGC GGGC 24

( 2 ) INFORMATION FOR SEQ ID NO:21:

( i ) SEQUENCE CHARACTERISTICS:
        ( A ) LENGTH: 35
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: POLY C PRIMER ( x i ) SEQUENCE DESCRIPTION: SEQ ID NO:21:

GCATGCGCGC GGCCGCGGAG GCCCCCCCCC CCCCC 35

( 2 ) INFORMATION FOR SEQ ID NO:22:

( i ) SEQUENCE CHARACTERISTICS:
        ( A ) LENGTH: 25
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: PRIMER B ( x i ) SEQUENCE DESCRIPTION: SEQ ID NO:22:

TGTGGCCAGG CATGCCAGTG TGGCC 25

( 2 ) INFORMATION FOR SEQ ID NO:23:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: PRIMER C ( x i ) SEQUENCE DESCRIPTION: SEQ ID NO:23:

GGTGTGGGAG AATTCTGCTT CTGA 24

( 2 ) INFORMATION FOR SEQ ID NO:24:

( i ) SEQUENCE CHARACTERISTICS:
        ( A ) LENGTH: 19
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: OLIGONUCLEOTIDE D ( x i ) SEQUENCE DESCRIPTION: SEQ ID NO:24:

TCTGCTTCTG ATGGCTCAA                                                                                            1 9

( 2 ) INFORMATION FOR SEQ ID NO:25:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 1, CLONE HBVT73,
            POSITION 251

( x i ) SEQUENCE DESCRIPTION: SEQ ID NO:25:

CCGCACAACA GTTCCCTGAC TTGC                                                                                      2 4

( 2 ) INFORMATION FOR SEQ ID NO:26:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 2, CLONE MOLT 4,
            POSITION 210

( x i ) SEQUENCE DESCRIPTION: SEQ ID NO:26:

GGCCACATAC GAGCAAGGCG TCGA                                                                                      2 4

( 2 ) INFORMATION FOR SEQ ID NO:27:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 3, CLONE DT259,
            POSITION 232*, THE 11TH NUCLEOTIDE CORRESPONDS TO
            MISMATCHES INTRODUCED RELATIVE TO THE NATURAL SEQUENCE ( x i ) SEQUENCE DESCRIPTION: SEQ ID NO:27:

CGCTTCTCCC GGATTCTGGA GTCC                                                                                      2 4

( 2 ) INFORMATION FOR SEQ ID NO:28:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 4, CLONE DT110,
            POSITION 257

( x i ) SEQUENCE DESCRIPTION: SEQ ID NO:28:

TTCCCATCAG CCGCCCAAAC CTAA                                                                                      24

( 2 ) INFORMATION FOR SEQ ID NO:29:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 5, CLONE VB12A1,
            POSITION 199*

( x i ) SEQUENCE DESCRIPTION: SEQ ID NO:29:

AGCTCTGAGC TGAATGTGAA CGCC                                                                                      24

( 2 ) INFORMATION FOR SEQ ID NO:30:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: THE V BETA 6, CLONE ATL12.2,
            POSITION 117, THE 18TH NUCLEOTIDE CORRESPONDS TO
            MISMATCHES INTRODUCED RELATIVE TO THE NATURAL SEQUENCE ( x i ) SEQUENCE DESCRIPTION: SEQ ID NO:30:

TCTCAGGTGT GATCCAAATT CGGG                                                                                      24

( 2 ) INFORMATION FOR SEQ ID NO:31:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 7, CLONE PL4.9,
            POSITION 169*

( x i ) SEQUENCE DESCRIPTION: SEQ ID NO:31:

CCTGAATGCC CCAACAGCTC TCTC                                                                                      24

( 2 ) INFORMATION FOR SEQ ID NO:32:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 8, CLONE PH11,
            POSITION 170

( x i ) SEQUENCE DESCRIPTION: SEQ ID NO:32:

CCATGATGCG GGGACTGGAG TTGC                                                                    2 4

( 2 ) INFORMATION FOR SEQ ID NO:33:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 9, CLONE PL2.6,
            POSITION 201*

( x i ) SEQUENCE DESCRIPTION: SEQ ID NO:33:

TTCCCTGGAG CTTGGTGACT CTGC                                                                    2 4

( 2 ) INFORMATION FOR SEQ ID NO:34:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 10, CLONE ATL12-1,
            POSITIN 299

( x i ) SEQUENCE DESCRIPTION: SEQ ID NO:34:

CCACGGAGTC AGGGGACACA GCAC                                                                    2 4

( 2 ) INFORMATION FOR SEQ ID NO:35:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 11, CLONE PL3.12,
            POSITION 297

( x i ) SEQUENCE DESCRIPTION: SEQ ID NO:35:

TGCCAGGCCC TCACATACCT CTCA                                                                    2 4

( 2 ) INFORMATION FOR SEQ ID NO:36:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 12, CLONE VBPH27,
            POSITION 109*, THE 14TH AND 23RD NUCLEOTIDES
            CORRESPOND TO MISMATCHES INTRODUCED RELATIVE TO THE

NATURAL SEQUENCE ( x i ) SEQUENCE DESCRIPTION: SEQ ID NO:36:

TGTCACCAGA CTGGGAACCA CCAC 24

( 2 ) INFORMATION FOR SEQ ID NO:37:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V BETA 13, CLONE CEM-VB1,
        POSITION 116, THE 7TH AND 12TH NUCLEOTIDES
        CORRESPOND TO MISMATCHES INTRODUCED RELATIVE TO THE
        NATURAL SEQUENCE ( x i ) SEQUENCE DESCRIPTION: SEQ ID NO:37:

CACTGCGGTG TACCCAGGAT ATGA 24

( 2 ) INFORMATION FOR SEQ ID NO:38:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V BETA 14, CLONE VBPH21,
        POSITION 175, THE 6TH AND 20TH NUCLEOTIDES
        CORRESPOND TO MISMATCHES INTRODUCED RELATIVE TO THE
        NATURAL SEQUENCE ( x i ) SEQUENCE DESCRIPTION: SEQ ID NO:38:

GGGCTCGGCT TAAGGCAGAC CTAC 24

( 2 ) INFORMATION FOR SEQ ID NO:39:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V BETA 15, CLONE ALT2-1,
        POSITIN 262

( x i ) SEQUENCE DESCRIPTION: SEQ ID NO:39:

CAGGCACAGG CTAAATTCTC CCTG 24

( 2 ) INFORMATION FOR SEQ ID NO:40:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V BETA 16, CLONE HBP42,
        POSITION 192*

( x i ) SEQUENCE DESCRIPTION: SEQ ID NO:40:

GCCTGCAGAA CTGGAGGATT CTGG                        24

( 2 ) INFORMATION FOR SEQ ID NO:41:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 17, CLONE VBPH29,
            POSITION 254

( x i ) SEQUENCE DESCRIPTION: SEQ ID NO:41:

CTGCTGAATT TCCCAAAGAG GGCC                        24

( 2 ) INFORMATION FOR SEQ ID NO:42:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 18, CLONE HUT102,
            POSITION 173*

( x i ) SEQUENCE DESCRIPTION: SEQ ID NO:42:

TGCCCCAGAA TCTCTCAGCC TCCA                        24

( 2 ) INFORMATION FOR SEQ ID NO:43:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA 19, CLONE HBVT02,
            POSITION 279

( x i ) SEQUENCE DESCRIPTION: SEQ ID NO:43:

TCCTCTCACT GTGACATCGG CCCA                        24

( 2 ) INFORMATION FOR SEQ ID NO:44:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
    ( A ) NAME/KEY:
    ( D ) OTHER INFORMATION: TYPE V BETA 20, CLONE HBVT72,
        POSITION 274

( x i ) SEQUENCE DESCRIPTION: SEQ ID NO:44:

TCTCAATGCC CCAAGAACGC ACCC 24

( 2 ) INFORMATION FOR SEQ ID NO:45:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA w21, CLONE IGRb01L,
            POSITION 318, THE 13TH AND 20TH NUCLEOTIDES
            CORRESPOND TO MISMATCHES INTRODUCED RELATIVE TO THE
            NATURAL SEQUENCE ( x i ) SEQUENCE DESCRIPTION: SEQ ID NO:45:

TCCAACCTGC AAGGCTTGAC GACT 24

( 2 ) INFORMATION FOR SEQ ID NO:46:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA w22, CLONE IGRb03,
            POSITION 110

( x i ) SEQUENCE DESCRIPTION: SEQ ID NO:46:

AAGTGATCTT GCGCTGTGTC CCCA 24

( 2 ) INFORMATION FOR SEQ ID NO:47:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V BETA w23, CLONE IGRa04,
            POSITION 155*

( x i ) SEQUENCE DESCRIPTION: SEQ ID NO:47:

GCAGGGTCCA GGTCAGGACC CCCA 24

( 2 ) INFORMATION FOR SEQ ID NO:48:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR (i i) MOLECULE TYPE: OLIGONUCLEOTIDE (i x) FEATURE:
    (A) NAME/KEY:
    (D) OTHER INFORMATION: TYPE V BETA w24, CLONE IGRa05,
    POSITION 95

(x i) SEQUENCE DESCRIPTION: SEQ ID NO:48:

CCCAGTTTGG AAAGCCAGTG ACCC 24

(2) INFORMATION FOR SEQ ID NO:49:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (D) OTHER INFORMATION: TYPE C BETA A, POSITION 71

(x i) SEQUENCE DESCRIPTION: SEQ ID NO:49:

GGTGTGGGAG AATTCTGCTT CTGA 24

(2) INFORMATION FOR SEQ ID NO:50:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (D) OTHER INFORMATION: TYPE C BETA B, POSITION 135

(x i) SEQUENCE DESCRIPTION: SEQ ID NO:50:

ACCAGCTCAG CTCCGCGGGG TCGG 24

(2) INFORMATION FOR SEQ ID NO:51:

(i) SEQUENCE CHARACTERISTICS:
        (A) LENGTH: 19
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (D) OTHER INFORMATION: TYPE C BETA C, POSITION 58

(x i) SEQUENCE DESCRIPTION: SEQ ID NO:51:

TCTGCTTCTG ATGGCTCAA 19

(2) INFORMATION FOR SEQ ID NO:52:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (i i) MOLECULE TYPE: OLIGONUCLEOTIDE ( i x ) FEATURE:
      ( A ) NAME/KEY:
      ( D ) OTHER INFORMATION: TYPE ACT 1, CLONE BETA-ACTIN,
          POSITION 1161

( x i ) SEQUENCE DESCRIPTION: SEQ ID NO:52:

ATTTGCGGTG GACGATGGAG GGGC　　　　　　　　　　　　　　　　　　　24

( 2 ) INFORMATION FOR SEQ ID NO:53:

( i ) SEQUENCE CHARACTERISTICS:
      ( A ) LENGTH: 24
      ( B ) TYPE: NUCLEOTIDE
      ( C ) STRANDEDNESS: SINGLE
      ( D ) TOPOLOGY: LINEAR ( i i ) MOLECULE TYPE: OLIGONUCLEOTIDE ( i x ) FEATURE:
      ( A ) NAME/KEY:
      ( D ) OTHER INFORMATION: TYPE ACT 2, CLONE BETA-ACTIN
          POSITION 261

( x i ) SEQUENCE DESCRIPTION: SEQ ID NO:53:

GGCATCGTCA CCAACTGGGA CGAC　　　　　　　　　　　　　　　　　　　24

( 2 ) INFORMATION FOR SEQ ID NO:54:

( i ) SEQUENCE CHARACTERISTICS:
      ( A ) LENGTH: 19
      ( B ) TYPE: NUCLEOTIDE
      ( C ) STRANDEDNESS: SINGLE
      ( D ) TOPOLOGY: LINEAR ( i i ) MOLECULE TYPE: OLIGONUCLEOTIDE ( i x ) FEATURE:
      ( A ) NAME/KEY:
      ( D ) OTHER INFORMATION: TYPE ACT 3, CLONE BETA ACTIN,
          POSITION 642

( x i ) SEQUENCE DESCRIPTION: SEQ ID NO:54:

ACCACCACGG CGGAGCGGG　　　　　　　　　　　　　　　　　　　　　　19

( 2 ) INFORMATION FOR SEQ ID NO:55:

( i ) SEQUENCE CHARACTERISTICS:
      ( A ) LENGTH: 24
      ( B ) TYPE: NUCLEOTIDE
      ( C ) STRANDEDNESS: SINGLE
      ( D ) TOPOLOGY: LINEAR ( i i ) MOLECULE TYPE: OLIGONUCLEOTIDE ( i x ) FEATURE:
      ( A ) NAME/KEY:
      ( D ) OTHER INFORMATION: TYPE C ALPHA E, POSITION 201

( x i ) SEQUENCE DESCRIPTION: SEQ ID NO:55:

GTTGCTCCAG GCCGCGGCAC TGTT　　　　　　　　　　　　　　　　　　　24

( 2 ) INFORMATION FOR SEQ ID NO:56:

( i ) SEQUENCE CHARACTERISTICS:
      ( A ) LENGTH: 24
      ( B ) TYPE: NUCLEOTIDE
      ( C ) STRANDEDNESS: SINGLE
      ( D ) TOPOLOGY: LINEAR ( i i ) MOLECULE TYPE: OLIGONUCLEOTIDE ( i x ) FEATURE:

(A) NAME/KEY:
        (D) OTHER INFORMATION: TYPE C ALPHA J, POSITION 12

(x i) SEQUENCE DESCRIPTION: SEQ ID NO:56:

CCCTGACCCT GCCGTGTACC AGCT 24

(2) INFORMATION FOR SEQ ID NO:57:

(i) SEQUENCE CHARACTERISTICS:
        (A) LENGTH: 19
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (D) OTHER INFORMATION: TYPE C ALPHA C, POSITION 57

(x i) SEQUENCE DESCRIPTION: SEQ ID NO:57:

GTCACTGGAT TTAGAGTCT 19

(2) INFORMATION FOR SEQ ID NO: 58:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (D) OTHER INFORMATION: TYPE V Alpha 1, THE 6TH AND 23RD
            NUCLEOTIDES CORRESPOND TO MISMATCHES INTRODUCED RELATIVE
            TO THE NATURAL SEQUENCE (x i) SEQUENCE DESCRIPTION: SEQ ID NO:58:

GGCATTAACG GTTTTGAGGC TGGA 24

(2) INFORMATION FOR SEQ ID NO: 59:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (D) OTHER INFORMATION: TYPE V Alpha 2, THE 24TH NUCLEOTIDE
            CORRESPONDS TO A MISMATCH INTRODUCED RELATIVE TO THE
            NATURAL SEQUENCE (x i) SEQUENCE DESCRIPTION: SEQ ID NO:59:

CAGTGTTCCA GAGGGAGCCA TTGC 24

(2) INFORMATION FOR SEQ ID NO: 60:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:

( A ) NAME/KEY:
                ( D ) OTHER INFORMATION: TYPE V Alpha 3

( x i ) SEQUENCE DESCRIPTION: SEQ ID NO:60:

CCGGGCAGCA GACACTGCTT CTTA 24

( 2 ) INFORMATION FOR SEQ ID NO: 61:

( i ) SEQUENCE CHARACTERISTICS:
                ( A ) LENGTH: 24
                ( B ) TYPE: NUCLEOTIDE
                ( C ) STRANDEDNESS: SINGLE
                ( D ) TOPOLOGY: LINEAR ( i i ) MOLECULE TYPE: OLIGONUCLEOTIDE ( i x ) FEATURE:
                ( A ) NAME/KEY:
                ( D ) OTHER INFORMATION: TYPE V Alpha 4

( x i ) SEQUENCE DESCRIPTION: SEQ ID NO:61:

TTGGTATCGA CAGCTTCCCT CCCA 24

( 2 ) INFORMATION FOR SEQ ID NO: 62:

( i ) SEQUENCE CHARACTERISTICS:
                ( A ) LENGTH: 24
                ( B ) TYPE: NUCLEOTIDE
                ( C ) STRANDEDNESS: SINGLE
                ( D ) TOPOLOGY: LINEAR ( i i ) MOLECULE TYPE: OLIGONUCLEOTIDE ( i x ) FEATURE:
                ( A ) NAME/KEY:
                ( D ) OTHER INFORMATION: TYPE V Alpha 5

( x i ) SEQUENCE DESCRIPTION: SEQ ID NO:62:

CGGCCACCCT GACCTGCAAC TATA 24

( 2 ) INFORMATION FOR SEQ ID NO: 63:

( i ) SEQUENCE CHARACTERISTICS:
                ( A ) LENGTH: 24
                ( B ) TYPE: NUCLEOTIDE
                ( C ) STRANDEDNESS: SINGLE
                ( D ) TOPOLOGY: LINEAR ( i i ) MOLECULE TYPE: OLIGONUCLEOTIDE ( i x ) FEATURE:
                ( A ) NAME/KEY:
                ( D ) OTHER INFORMATION: TYPE V Alpha 6

( x i ) SEQUENCE DESCRIPTION: SEQ ID NO:63:

TCCGCCAACC TTGTCATCTC CGCT 24

( 2 ) INFORMATION FOR SEQ ID NO: 64:

( i ) SEQUENCE CHARACTERISTICS:
                ( A ) LENGTH: 24
                ( B ) TYPE: NUCLEOTIDE
                ( C ) STRANDEDNESS: SINGLE
                ( D ) TOPOLOGY: LINEAR ( i i ) MOLECULE TYPE: OLIGONUCLEOTIDE ( i x ) FEATURE:
                ( A ) NAME/KEY:
                ( D ) OTHER INFORMATION: TYPE V Alpha 7, THE 9TH AND 15TH
                        NUCLEOTIDES CORRESPOND TO MISMATCHES INTRODUCED RELATIVE
                        TO THE NATURAL SEQUENCE ( x i ) SEQUENCE DESCRIPTION: SEQ ID NO:64:

GCAACATGCT GGCGGAGCAC CCAC 24

( 2 ) INFORMATION FOR SEQ ID NO: 65:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 8

( x i ) SEQUENCE DESCRIPTION: SEQ ID NO:65:

CATTCGTTCA AATGTGGGCA AAAG 24

( 2 ) INFORMATION FOR SEQ ID NO: 66:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 9, THE 22ND NUCLEOTIDE
            CORRESPONDS TO A MISMATCH INTRODUCED RELATIVE TO THE
            NATURAL SEQUENCE ( x i ) SEQUENCE DESCRIPTION: SEQ ID NO:66:

CCAGTACTCC AGACAACGCC TGCA 24

( 2 ) INFORMATION FOR SEQ ID NO: 67:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 10

( x i ) SEQUENCE DESCRIPTION: SEQ ID NO:67:

CACTGCGGCC CAGCCTGGTG ATAC 24

( 2 ) INFORMATION FOR SEQ ID NO: 68:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 11

( x i ) SEQUENCE DESCRIPTION: SEQ ID NO:68:

CGCTGCTCAT CCTCCAGGTG CGGG 24

( 2 ) INFORMATION FOR SEQ ID NO: 69:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 12

( x i ) SEQUENCE DESCRIPTION: SEQ ID NO:69:

TCGTCGGAAC TCTTTTGATG AGCA 24

( 2 ) INFORMATION FOR SEQ ID NO: 70:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 13

( x i ) SEQUENCE DESCRIPTION: SEQ ID NO:70:

TTCATCAAAA CCCTTGGGGA CAGC 24

( 2 ) INFORMATION FOR SEQ ID NO: 71:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 14

( x i ) SEQUENCE DESCRIPTION: SEQ ID NO:71:

CCCAGCAGGC AGATGATTCT CGTT 24

( 2 ) INFORMATION FOR SEQ ID NO: 72:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 15, THE 12TH NUCLEOTIDE
            CORRESPONDS TO A MISMATCH INTRODUCED RELATIVE TO THE
            NATURAL SEQUENCE ( x i ) SEQUENCE DESCRIPTION: SEQ ID NO:72:

TTGCAGACAC CGAGACTGGG GACT 24

( 2 ) INFORMATION FOR SEQ ID NO: 73:

( i ) SEQUENCE CHARACTERISTICS:
            ( A ) LENGTH: 24
            ( B ) TYPE: NUCLEOTIDE
            ( C ) STRANDEDNESS: SINGLE
            ( D ) TOPOLOGY: LINEAR ( i i ) MOLECULE TYPE: OLIGONUCLEOTIDE ( i x ) FEATURE:
            ( A ) NAME/KEY:
            ( D ) OTHER INFORMATION: TYPE V Alpha 16

( x i ) SEQUENCE DESCRIPTION: SEQ ID NO:73:

TCAACGTTGC TGAAGGGAAT CCTC 24

( 2 ) INFORMATION FOR SEQ ID NO: 74:

( i ) SEQUENCE CHARACTERISTICS:
            ( A ) LENGTH: 24
            ( B ) TYPE: NUCLEOTIDE
            ( C ) STRANDEDNESS: SINGLE
            ( D ) TOPOLOGY: LINEAR ( i i ) MOLECULE TYPE: OLIGONUCLEOTIDE ( i x ) FEATURE:
            ( A ) NAME/KEY:
            ( D ) OTHER INFORMATION: TYPE V Alpha 17, THE 12TH NUCLEOTIDE
                   CORRESPONDS TO A MISMATCH INTRODUCED RELATIVE TO THE
                   NATURAL SEQUENCE ( x i ) SEQUENCE DESCRIPTION: SEQ ID NO:74:

TGGGAAAGGC CGTGCATTAT TGAT 24

( 2 ) INFORMATION FOR SEQ ID NO: 75:

( i ) SEQUENCE CHARACTERISTICS:
            ( A ) LENGTH: 24
            ( B ) TYPE: NUCLEOTIDE
            ( C ) STRANDEDNESS: SINGLE
            ( D ) TOPOLOGY: LINEAR ( i i ) MOLECULE TYPE: OLIGONUCLEOTIDE ( i x ) FEATURE:
            ( A ) NAME/KEY:
            ( D ) OTHER INFORMATION: TYPE V Alpha 18

( x i ) SEQUENCE DESCRIPTION: SEQ ID NO:75:

CAGCACCAAT TTCACCTGCA GCTT 24

( 2 ) INFORMATION FOR SEQ ID NO: 76:

( i ) SEQUENCE CHARACTERISTICS:
            ( A ) LENGTH: 24
            ( B ) TYPE: NUCLEOTIDE
            ( C ) STRANDEDNESS: SINGLE
            ( D ) TOPOLOGY: LINEAR ( i i ) MOLECULE TYPE: OLIGONUCLEOTIDE ( i x ) FEATURE:
            ( A ) NAME/KEY:
            ( D ) OTHER INFORMATION: TYPE V Alpha 19

( x i ) SEQUENCE DESCRIPTION: SEQ ID NO:76:

ACACTGGCTG CAACAGCATC CAGG 24

( 2 ) INFORMATION FOR SEQ ID NO: 77:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 20

( x i ) SEQUENCE DESCRIPTION: SEQ ID NO:77:

TCCCTGTTTA TCCCTGCCGA CAGA        24

( 2 ) INFORMATION FOR SEQ ID NO: 78:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 21

( x i ) SEQUENCE DESCRIPTION: SEQ ID NO:78:

AGCAAAATTC ACCATCCCTG AGCG        24

( 2 ) INFORMATION FOR SEQ ID NO: 79:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha 22

( x i ) SEQUENCE DESCRIPTION: SEQ ID NO:79:

CCTGAAAGCC ACGAAGGCTG ATGA        24

( 2 ) INFORMATION FOR SEQ ID NO: 80:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha w23

( x i ) SEQUENCE DESCRIPTION: SEQ ID NO:80:

TGCCTCGCTG GATAAATCAT CAGG        24

( 2 ) INFORMATION FOR SEQ ID NO: 81:

( i ) SEQUENCE CHARACTERISTICS:
        ( A ) LENGTH: 24

( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha w24, THE 21ST NUCLEOTIDE
            CORRESPONDS TO A MISMATCH INTRODUCED RELATIVE TO THE
            NATURAL SEQUENCE ( x i ) SEQUENCE DESCRIPTION: SEQ ID NO:81:

CTGGATGCAG ACACAAAGCA GAGC 24

( 2 ) INFORMATION FOR SEQ ID NO: 82:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha w25, THE 7TH AND 17TH
            NUCLEOTIDES CORRESPOND TO MISMATCHES INTRODUCED RELATIVE
            TO THE NATURAL SEQUENCE ( x i ) SEQUENCE DESCRIPTION:SEQ ID NO:82:
                TGGCTACGGT ACAAGCCGGA CCCT ( 2 ) INFORMATION FOR SEQ ID NO: 83:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha w26, THE 4TH AND 20TH
            NUCLEOTIDES CORRESPOND TO MISMATCHES INTRODUCED RELATIVE
            TO THE NATURAL SEQUENCE ( x i ) SEQUENCE DESCRIPTION: SEQ ID NO:83:

AGCGCAGCCA TGCAGGCATG TACC 24

( 2 ) INFORMATION FOR SEQ ID NO: 84:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha w27

( x i ) SEQUENCE DESCRIPTION: SEQ ID NO:84:

AAGCCCGTCT CAGCACCCTC CACA 24

( 2 ) INFORMATION FOR SEQ ID NO: 85:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha w28, THE 8TH AND 15TH
            NUCLEOTIDES CORRESPOND TO MISMATCHES INTRODUCED RELATIVE
            TO THE NATURAL SEQUENCE ( x i ) SEQUENCE DESCRIPTION: SEQ ID NO:85:

TGGTTGTGCA CGAGCGAGAC ACTG 24

( 2 ) INFORMATION FOR SEQ ID NO: 86:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE V Alpha w29

( x i ) SEQUENCE DESCRIPTION: SEQ ID NO:86:

GAAGGGTGGA GAACAGATGC GTCG 24

( 2 ) INFORMATION FOR SEQ ID NO: 87:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE C Alpha A ( x i ) SEQUENCE DESCRIPTION: SEQ ID NO:87:

ATACACATCA GAATTCTTAC TTTG 24

( 2 ) INFORMATION FOR SEQ ID NO: 88:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( D ) OTHER INFORMATION: TYPE C Alpha B ( x i ) SEQUENCE DESCRIPTION: SEQ ID NO:88:

GTTGCTCCAG GCCGCGGCAC TGTT 24